United States Patent [19]
Theil

[11] Patent Number: 5,834,199
[45] Date of Patent: Nov. 10, 1998

[54] METHODS OF IDENTIFYING TRANSITION METAL COMPLEXES THAT SELECTIVELY CLEAVE REGULATORY ELEMENTS OF MRNA AND USES THEREOF

[75] Inventor: Elizabeth C. Theil, Raleigh, N.C.

[73] Assignee: North Carolina State University, Raleigh, N.C.

[21] Appl. No.: 841,166

[22] Filed: Apr. 29, 1997

[51] Int. Cl.[6] .................................................. C12Q 1/68
[52] U.S. Cl. ......................... 435/6; 435/91.1; 435/91.2; 436/501; 514/1; 514/183; 514/184; 514/185; 514/188; 536/23.1; 536/24.1; 536/24.3; 536/24.31; 536/24.32; 536/24.33; 536/25.3; 935/77; 935/78
[58] Field of Search ................... 435/5, 6, 91.1, 435/91.2, 810; 436/501; 536/22.1, 23.1, 24.1, 24.3–24.33, 25.3; 935/77, 78; 514/1, 183, 184, 185, 188

[56] References Cited

U.S. PATENT DOCUMENTS

| | | | |
|---|---|---|---|
| 5,270,163 | 12/1993 | Gold et al. | 435/6 |
| 5,439,794 | 8/1995 | Barton | 435/6 |
| 5,475,096 | 12/1995 | Gold et al. | 536/23.1 |
| 5,503,978 | 4/1996 | Schneider et al. | 435/6 |
| 5,567,588 | 10/1996 | Gold et al. | 435/6 |
| 5,595,877 | 1/1997 | Gold et al. | 435/6 |

FOREIGN PATENT DOCUMENTS

WO 95/29924  11/1995  WIPO .

OTHER PUBLICATIONS

Balla et al. (1992) J. Biol. Chem. 267:18148–53.
Bhasker et al. (1993) J. Biol. Chem. 268:12699–705.
Butt et al. (1996) Proc. Natl. Acad. Sci. 93:4345–9.
Cairo et al. (1985) Biochem. Biophys. Res. Comm. 133:314–21.
Carter et al. (1990) Proc. Natl. Acad. Sci. USA 87:9373–7.
Cheng et al. (1995) J. Am. Chem. Soc. 117:2970–80.
Chow et al. (1992) Biochem. 31:3534–42.
Dickey et al. (1987) J. Biol. Chem. 262–7901–7.
Dickey et al. (1988) J. Biol. Chem. 263:3071–4.
Didsbury et al. (1986) J. Biol. Chem.261:949–55.
Dix et al. (1993) J. Mol. Biol. 231:230–40.
Dix et al. (1992) Biochemistry 31:2818–22.
Dupureur et al. (1996) In: Comprehensive Supramolecular Chem., Suslick KS (ed.), vol. 5, Pergamon Press, Elsevier, Oxford, pp. 295–316.
Franz et al. (1990) Biochem. 29:4747–51.
Girelli et al. (1995) Blood 86:4050–3.
Girelli et al. (1995) Brit. J. Haematology 90:931–4.
Gold, L. (1995) J. Biol. Chem. 270:13581–4.
Gold, et al.(1995) Ann. Rev. Biochem. 64:763–97.
Goyne et al. (1987) J. Am. Chem. Soc. 109:2846–8.
Guo et al. (1994) J. Biol. Chem. 268:24252–60.
Harrell et al. (1991) Proc. Natl. Acad. Sci. USA 88:4166–70.
Henderson et al. (1994) J. Biol. Chem. 269:17481–9.
Hermann et al. (1995) RNA 1:1009–17.
Iwai et al. (1995) EMBO J. 14:5350–57.
Jenison et al. (1994) Science 263:1425–9.
Klausner et al. (1993) Cell 72:19–28.
Lam et al. (1995) Biometals 8:290–6.
Liebold et al. (1992) Ann. Rev. Nutr. 12:345–68.
Lim et al. (1993) Biochemistry 32:11029–34.
Melefors et al.(1993) J. Biol. chem. 268:5974–8.
Methot et al. (1996) RNA 2:38–50.
Murakawa et al. (1989) Nucl. Acids Res. 17:5361–75.

(List continued on next page.)

Primary Examiner—Ardin H. Marschel
Attorney, Agent, or Firm—Klauber & Jackson

[57] ABSTRACT

Methods for selecting transition metal complexes (TMCs) that can modulate the translation of an mRNA by selectively cleaving a regulatory element of the mRNA are described. Included are in vitro, in situ, and/or in vivo methods. In addition, methods of identifying and characterizing mRNAs that contain regulatory elements which can be targeted by the TMCs of the present invention are also provided. Pharmaceutical compositions containing the TMCs of the present invention are also included.

23 Claims, 6 Drawing Sheets

OTHER PUBLICATIONS

Neyhart et al. (1995) J. Am. Chem. Soc. 117:1463–71.
Pogozelski et al. (1995) J. Am. Chem. Soc. 117:6428–33.
Pratviel et al. (1995) Angew. Chem. Int. Ed. Engl. 34:746–69.
Ragland et al. (1993) Plant Mol. Biol. 21:555–60.
Shull et al. (1982) J. Biol. Chem. 257:14187–91.
Sierzputowska–Gracz et al. (1995) Nucl. Acids Res. 23:145–52.
Sigman (1986) Acc. Chem. Res. 19:180–186.
Sitlani et al. (1992) J. Am. Chem. Soc. 114:2303–12.
Stubbe et al. (1987) Chem. Rev. 87:1107–36.
Theil, E.C. (1990) J. Biol. Chem. 265:4771–4.
Theil, E.C. (1993) Biofactors 4:87–93.
Theil, E.C. (1994) Biochem. J. 304:1–11.
Theil, E.C. (1994) New J. Chem. 18:435–41.
Thorp et al. (1996) Inorganic Chem. 35:2773–9.
Tuerk et al. (1990) Science 249:505–10.
Wang et al. (1990) Nucl. Acids Res. 18:4463–8.
Weiss et al. (1994) In: Prog. Iron Res., Hershko et al. ed., Plenum Press, NY, pp. 133–139.
Yang et al. (1996) Science 272:1343–7.

FIG. 4B

FERRITIN-IRE / TTR-IREc

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( x i ) SEQUENCE DESCRIPTION: SEQ ID NO:1:

GAGUGAGUAG AGUUCUUGCU UCAACAGUGU UUGAACGGAA CCCUCUCUCU C      51

( 2 ) INFORMATION FOR SEQ ID NO:2:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i x ) FEATURE:
        ( A ) NAME/KEY: N at Position 20 is either a C or a U ( x i ) SEQUENCE DESCRIPTION: SEQ ID NO:2:

CCCGCGGGUC UGUCUCUUGN UCAACAGUGU UUGACGAACA GAUCCGGGG      49

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( x i ) SEQUENCE DESCRIPTION: SEQ ID NO:3:

GAUUAUCGGG AGCAGUGUCU UCCAUAAUC      29

( 2 ) INFORMATION FOR SEQ ID NO:4:

( i ) SEQUENCE CHARACTERISTICS:
        ( A ) LENGTH: 49 base pairs
        ( B ) TYPE: nucleic acid
        ( C ) STRANDEDNESS: single (D) TOPOLOGY: linear (ii) MOLECULE TYPE: mRNA (iii) HYPOTHETICAL: NO (xi) SEQUENCE DESCRIPTION: SEQ ID NO:4:

GAGUGAGUAG AGUUCUUGCU UCACAGUGUU GAACGGAACC CUCUCUCUC    49

(2) INFORMATION FOR SEQ ID NO:5:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (xi) SEQUENCE DESCRIPTION: SEQ ID NO:5:

CUCUGAGUAG AGUUCUUGCU UCACAGUGUU GAACGGAACC CUCUCUCUC    49

(2) INFORMATION FOR SEQ ID NO:6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (xi) SEQUENCE DESCRIPTION: SEQ ID NO:6:

GAGUGAGUAG AGUUCUGUUC CAGUGUUGAA CGGAACCCUC UCUCUC    46

(2) INFORMATION FOR SEQ ID NO:7:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (xi) SEQUENCE DESCRIPTION: SEQ ID NO:7:

GAGUGAGUAG AGUUCUUGCU UCACAGUAUU GAACGGAACC CUCUCUCUC    49

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (xi) SEQUENCE DESCRIPTION: SEQ ID NO:8:

GUUCUUGCUU CAACAGUGUU UGAACGGAAC    30

(2) INFORMATION FOR SEQ ID NO:9:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: mRNA ( i i i ) HYPOTHETICAL: NO ( x i ) SEQUENCE DESCRIPTION: SEQ ID NO:9:

GAUUAUCGGG AGCAGUGUCU UCCAUAAUC                                                         2 9

( 2 ) INFORMATION FOR SEQ ID NO:10:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: mRNA ( i i i ) HYPOTHETICAL: NO ( x i ) SEQUENCE DESCRIPTION: SEQ ID NO:10:

CCUUCAGCUC GUGUAGCUCA UUAGCUCCGA GCUCCCUA                                               3 8

METHODS OF IDENTIFYING TRANSITION METAL COMPLEXES THAT SELECTIVELY CLEAVE REGULATORY ELEMENTS OF MRNA AND USES THEREOF

GOVERNMENTAL SUPPORT

The research leading to the present invention was supported, in part, by a grant from the National Institutes of Health, Grant No. RO1 DK20251. Accordingly, the Government may have certain rights in the invention.

FIELD OF THE INVENTION

The invention relates generally to providing new methods of developing new drugs that inactivate regulatory elements found on mRNAs. More particularly, the invention provides methods of obtaining transition metal complexes that can deregulate the expression of an mRNA with specificity, through cleavage of regulatory elements on the mRNA.

BACKGROUND OF THE INVENTION mRNA-dependent variations in rates of protein synthesis are important in the competition between stress and normal mRNAs, the competition between viral and host mRNAs, the temporal variation during development of the production of various gene products, and for responses to environmental changes such as light intensity in plants and iron in animals. The range of the three-dimensional structures which can be assumed by single-stranded mRNA is greater than for double-stranded DNA, indicating the great potential for specificity of drugs targeted to RNA. The most studied mRNA regulatory sequences are the iron responsive elements (IREs), found in the non-coding regions of mRNAs encoding at least three of the proteins of iron metabolism. [Theil, *J. Biol. Chem.* 265: 4771–4774 (1990); Theil et al., *Biofactors*, 4: 8–93 (1993); Klausner et al., *Cell*, 72: 19–28 (1993)]. Studies of the posttranscriptional regulation of ferritin, as well as of the transferrin receptor-IRE and erythroid aminolevulinate synthetase (eALAS-IRE) have been identified and demonstrate the role of the conserved, noncoding regulatory element, the IRE, in controlling the synthesis of the proteins encoded in the mRNAs [Klausner et al., 1993, supra; Theil, 1990, supra; Theil, *Biochem. J.*, 304: 1–11 (1994a); Liebold and Gua, *Ann. Rev. Nutr.*, 12: 345–368 (1992); Hentze, *Adv. Exp. Med.*, 356: 119–126 (1995)]. mRNAs from higher organisms are composed of three sections: the coding region, which is translated into protein, and two noncoding sections which flank the coding section and are called the 5' or 3' untranslated region (UTR). mRNAs are translated in the 5' to 3' direction where 5' or 3' refer to the free ribose hydroxyl that occurs at the polyribonucleotide chain ends. Often, but not exclusively, the 5' UTR influences the translation rate and the 3' UTR influences the mRNA turnover rates, i.e., mRNA stability. Effects of sequences in the 5' UTR of mRNA on rates of protein synthesis/mRNA translation can be divided into two types: negative control e.g., diminished binding of initiation factors/ribosomes, and positive control e.g., enhanced binding of initiation factors/ribosomes.

Specific non-coding DNA sequences have long been known to control the rates of RNA synthesis/DNA transcription in either a positive or a negative manner. Such sequences are called cis elements. Proteins which bind to the specific DNA sequences are called trans factors. mRNAs also contains cis elements that are regulatory elements. Currently, cis elements in mRNA are less well defined than their DNA counterparts. However, in the case of the mRNA encoding the iron storage protein, ferritin, conservation of translational control sequences in the 5' UTR of mRNAs from a wide spectrum of animals is so high, ~97%, that such definition is apparent [Theil, 1990, supra; Theil et al., 1993, supra].

The regulatory element in ferritin mRNA is called the IRE (iron responsive element) because cellular iron in animals can regulate the function. The IRE decreases translation rates, when iron is low, through interactions with a specific binding protein, or trans factor known as the IRP. A variant of the ferritin IRE in the mRNA for erythroid aminolevulinate synthetase, (eALAS), the enzyme involved in the first step in heme biosynthesis, also binds the IRP which serves to block translation [Bhasker et al., *J. Biol. Chem.* 268: 12699–12704 (1993); Melefors et al., *J. Biol. Chem.* 268: 5974–5978 (1993)].

Another variant of the IRE acts as stability element in the 3' UTR of the mRNA which encodes the transferrin receptor, (TfR), a protein involved in iron uptake [Klausner et al., 1993, supra]. Such stability elements regulate the rate of mRNA turnover. For example, when iron is low, the IRP protects TfR mRNA so that transferrin receptor is synthesized and iron uptake can be facilitated. From their varied roles, it is clear that regulatory elements of animal mRNAs must have remarkably specific structures to coordinately regulate the synthesis of proteins involved, as exemplified by IREs of the mRNAs encoding the proteins involved in iron storage, uptake and utilization. The regulatory elements of mRNAs are susceptible to nucleic acid cleavage by naturally occurring nucleases, as well as by artificial compounds. For example, transition metal complexes (TMCs) can function as nucleases under a wider range of reaction conditions than the naturally occurring protein nucleases. Free radical cleavage, facilitated by the metal in the coordination complexes, generally occurs at or near the site of ligand binding. TMCs were used originally to probe the ferritin IRE in vitro because the IRE region was so unreactive with more classical probes that even determining the IRP "footprint" was difficult (only 1–2 reactive sites/30 nucleotides). The sizes of the binding/cleaving radicals used so far have varied from ~2Å to 13Å. Fortuitously, the TMCs used to date have "fit" different substructures of the IRE region and have been used to show the effect of mutations on structure in the hairpin loop, the internal loop, the upper stem and the base-paired flanking regions (FIG. 1, Table 1). In addition, TMCs have emphasized the folded structure of the IRE (RNA self protection from hydroxyl radical cleavage) [Harrell et al., *Proc. Natl. Acad. Sci. USA*, 88: 4166–4170 (1991)], alternate IRE conformations [Wang et al., *Nucl. Acids Res.*, 18: 4463–4468 (1990)] and shown the IRP "footprint" [Harrell et al., 1991, supra].

Transition metal complexes with heteroaromatic organic ligands have rigid, three dimensional shapes which can bind to nucleic acids. The shapes and sizes of the TMCs can be altered by synthesis with the potential of increasing specificity for particular nucleic acid target sites [Dupureur and Barton, in *Comprehensive Supramolecular Chemistry*, Suslick KS (ed.), Vol. 5, Pergamon Press, Elsevier, Oxford, pp. 295–316 (1996)]. When the metal in a TMC is redox active, oxidizing radicals are produced which cleave the nucleic acids at or near the site of binding to the DNA or RNA. The oxidation of nucleic acids by TMCs can occur via a variety of chemical mechanisms [Pratviel et al., *Angew. Chem. Int. Ed. Engl.*, 34: 746–769 (1995); Stubbe and Kozarich, *Chem. Rev.*, 87: 1107–1136 (1987)]. The Carbon-Hydrogen bonds of the sugar functionalities of the nucleic acids are sufficiently weak for activation by a wide range of transition-metal oxidants. The pathways for oxidation of DNA have been delineated in many cases e.g., Cu-phen cleaves DNA by oxidation of the 1' and 4' hydrogens [Goyne and Sigman, *J. Am. Chem. Soc.*, 109: 2846–2848 (1987)], Ru(tpy)(bpy)$O^{2+}$ cleaves DNA by oxidation of the 1' hydrogen only [Cheng et al., *J. Am. Chem. Soc.*, 117: 2970–2980 (1995)], Rh(phen)$_2$(phi)$^{3+}$ cleaves DNA by oxidation of the 3' hydrogen [Sitlani et al., *J. Am. Chem. Soc.*, 114: 2303–2312 (1992)], and •OH radical generated by Fe(EDTA)$_2$- activates all of the C—H bonds with some preference for 4' and 5' in duplex DNA [Pogozelski et al., *J. Am. Chem. Soc.*, 117: 6428–6433]. That these are the pathways was confirmed by detecting release of free base and the furanone product 5-MF by GC-MS [Goyne and Sigman, 1987, supra] and by HPLC [Cheng et al., 1995, supra]. While the pathways for sugar oxidation in RNA is currently not as well defined, sugar oxidation by TMCs has advantages over base oxidation for structural specificity because all four nucleotides exhibit similar reactivity; thus, the contribution of overall structure to the binding site is potentially larger.

mRNA regulatory elements can play an important role in protein synthesis. IREs, for example, are involved in the regulation of the synthesis of at least three key proteins involved in iron metabolism. The increased expression of these proteins is therapeutically useful in the treatment of diseases such as thalassemia and sickle cell anemia, where transfusional iron overload can limit effective management of these diseases. Increased expression of such proteins could similarly relieve an iron overload that otherwise could lead to tissue damage in hemochromatosis.

More particularly, when iron is in excess of cellular or body need, or during inflammation and infection, stable ferritin mRNAs are derepressed. The stable ferritin mRNA is translated and ferritin is synthesized in larger amounts to detoxify the excess iron. Although ferritin synthesis increases, the amount of iron to be handled can exceed ferritin capacity which can result in toxic consequences. One approach to diminish the iron toxicity is to enhance ferritin synthesis by altering the IRE before the iron burdens increase. Such an approach, for example, would lead to a potentially more positive outcome for long-term transfusion therapy. The principle that "prophylactic" synthesis of ferritin can be advantageous has been illustrated in cultured endothelial cells where accumulated ferritin protected the cells against oxygen toxicity [Balla et al., *J. Biol. Chem.*, 267: 18148–18153 (1992)]. Hyperferritinemia itself is relatively benign compared to iron overload, based on the recent description of the Verona mutation in which an L-ferritinemia occurs related to a genetic mutation in the IRE [Girelli et al., *Brit. J. Haematology*, 90: 931–934 (1995a)]. Furthermore, ferritin mRNA with an inactive/deleted IRE appears to be stable and functional, even without a cap, based on data obtained both in vitro [Dickey et al., *J. Biol. Chem.* 263: 3071–3074 (1988); Dix et al., *Biochemistry*, 31: 2818–2822 (1992)] as well as being active in vivo [Girelli et al., *Blood*, 86: 4050–4053 (1995b)]. Thus, there is a need to provide methods for obtaining new drugs that can override the regulatory effect of the ferritin IRE during the treatment of specific diseases, and thereby increase the rate of ferritin synthesis. More generally, there is a need to provide methods of identifying new agents that can deregulate the expression of a protein with specificity when desired for a clinical purpose, by specifically disabling the regulatory element of the mRNA encoding that protein. Further, there is a need to identify new mRNAs that contain regulatory elements which can be cleaved by a TMC, thereby identifying new targets for TMC manipulation of the expression of specific proteins.

The citation of any reference herein should not be construed as an admission that such reference is available as "Prior Art" to the instant application.

SUMMARY OF THE INVENTION

The present invention provides methods for selecting transition metal complexes (TMCs) that can modulate the translation of an mRNA by selectively cleaving a regulatory element of the mRNA. The TMCs comprise an organic ligand and an oxidative metal. Regulatory elements modulate the translation of mRNAs by functioning as a regulatory site for the translation of the mRNA. A selected TMC cleaves an elected regulatory element, therein impairing the function of the regulatory element as a regulatory site, and thereby modulating the translation of the mRNA. The TMCs are selected on the basis of their capacity to cleave a specific regulatory element, and more importantly, for their particular specificity in catalyzing the cleavage. In one particular embodiment, the organic ligand of the TMC is either a phenanthroline or a phenanthroline derivative. In another particular embodiment, the regulatory element is an iron response element (IRE) or more particularly, a ferritin IRE.

One aspect of the present invention includes in vitro methods for selecting TMCs that can modulate the translation of an mRNA by selectively cleaving a regulatory element of the mRNA. One such method includes contacting a TMC with an mRNA that has a regulatory element, and then determining whether the translation of the mRNA is modulated and/or whether the regulatory element is selectively cleaved by the TMC. A TMC is selected that modulates the translation of the mRNA and/or selectively cleaves the regulatory element. The modulation of the translation of the mRNA leads to either a facilitation of the translation of the mRNA, or in the alternative, to the prevention or diminution of the translation of the mRNA. In either case, such modulation of the translation of the mRNA results in a corresponding increase or decrease respectively, in the amount of protein expressed by the mRNA.

A related aspect of the present invention includes methods for selecting TMCs that can modulate the translation of an mRNA by selectively cleaving an elected regulatory element of the mRNA in situ and/or in vivo. In preferred embodiments of this type the mRNA is modulated in a eukaryotic cell. In one such embodiment, the eukaryotic cell is an embryonic tadpole red cell. In another embodiment, the eukaryotic cell is a mammalian cell. In a preferred embodiment of this particular type, the mammalian cell is a HeLa cell.

In one embodiment of this aspect of the invention, the method comprises contacting a candidate TMC with a eukaryotic cell that contains an mRNA (e.g., a target RNA) that has the elected regulatory element. The method includes determining a cleavage activity of the candidate TMC for the mRNA that is a measure of its ability to cleave the elected regulatory element; determining the degree of disruption by the TMC on normal cellular function in the eukaryotic cell; and then correlating the cleavage activity of the TMC with the degree of disruption of the normal cellular function. Such a correlation enables the selection of a TMC that has a maximal cleavage activity in a eukaryotic cell, while causing a minimal degree of disruption.

In one such embodiment determining said cleavage activity is performed by determining the amount of protein expressed by the mRNA (i.e., the target mRNA). In this case correlating the cleavage activity with the degree of disruption is performed by correlating the amount of protein expressed with the degree of disruption. The amount of protein expressed by the (target) mRNA will either increase or decrease after treatment with the TMC, depending on the regulatory element that is cleaved, and the specific site of cleavage. In one one embodiment of this type, the protein expressed by the (target) mRNA is a marker protein. In a particular embodiment the marker protein is β-galactosidase.

The degree of disruption of a normal cellular function is determined by evaluating a properties of the eukaryotic cell, such as a determination of cellular poly $A^+$ integrity, or a determination of the cellular DNA integrity. In addition, the degree of disruption of a normal cellular function can be determined by quantifying cellular protein synthesis, or by quantifying cell growth. The degree of disruption of a normal cellular function can be determined by evaluating cell viability as determined as a percentage of trypan blue exclusion. Alternatively two or more of these determinations are performed to assess the degree of disruption.

A further aspect of the present invention includes methods for selecting TMCs that can modulate the translation of an mRNA by selectively cleaving an elected regulatory element of the mRNA in vivo, i.e., in a non-human animal. The non-human animal contains an mRNA that comprises the regulatory element, and a TMC is selected on the basis of its ability to cleave the elected regulatory element and/or alter the rate of expression of the mRNA, while causing a minimum of disruption of a normal cellular function in the non-human animal. The alteration of the rate of expression of the mRNA that contains the regulatory element, and the degree of disruption of a normal cellular function in the non-human animal is determined either by the same parameters as for eukaryotic cells or by general measurements such as in the amount of food intake, growth, development and the like.

In one particular embodiment, a TMC is chosen to be administered to a non-human animal that contains an mRNA which comprises the elected regulatory element. The specificity of the chosen TMC to cleave the elected regulatory element relative to its disruption of a normal cellular function in the non-human animal is then determined. A selected TMC is selected on the basis of its ability to cleave the elected regulatory element while causing a minimum of disruption of the normal cellular functions in the non-human animal. A method of this aspect of the present invention can be performed alone, or in conjunction with an in situ method and/or in vitro method of the present invention. Generally, the in 30 vitro method will be performed prior to the in situ method, which in turn, is performed prior to the in vivo method.

A non-human animal of the present invention is preferably a non-human mammal. In one particular embodiment, the non-human mammal is a rodent. In one such preferred embodiment, the rodent is a mouse.

One general method for identifying a TMC that can modulate the translation of an mRNA by selectively cleaving a regulatory element of the mRNA comprises contacting a TMC with an mRNA containing an elected regulatory element, and an mRNA containing a control regulatory element, and then determining in vitro the relative specificity of the TMC for cleaving the elected regulatory element in comparison to cleaving the control regulatory element. A candidate TMC is selected over an alternative TMC on the basis of the candidate TMC having a higher specificity for cleaving the elected regulatory element in comparison to cleaving the control regulatory element, relative to the alternative TMC. A selected candidate TMC can then be further selected for in another in vitro method of the present invention, or alternatively, in an in situ or an in vivo method of the present invention. Alternatively, this method can be carried out in situ or in vivo, provided that an mRNA containing the elected regulatory element and an mRNA containing the control regulatory element are contained by the cell, and the non-human animal respectively.

In one such particular embodiment the elected regulatory element is a first iron response element (IRE) and the control regulatory element is a second IRE. Because several IREs have been identified, such IREs may be used as control regulatory elements, as exemplified herein. In one such embodiment the control IRE is a transferrin receptor IRE. However, the present invention is not limited to such control regulatory elements, since any defined regulatory element may also be used as a control regulatory element in the methods of the present invention. Similarly, an elected regulatory element can be an IRE. In one embodiment the elected IRE is a ferritin IRE. In an embodiment of this type the ferritin IRE is either an H-ferritin IRE and or an L-ferritin IRE. Such a ferritin IRE can include the ferritin specific, base paired IRE flanking region.

Another general method for identifying a TMC that can modulate the translation of an mRNA by selectively cleaving a regulatory element of the mRNA comprises contacting a TMC with an mRNA containing an elected regulatory element, and contacting the TMC with a control nucleic acid. The relative specificity of the TMC for cleaving the elected regulatory element in comparison to cleaving the control nucleic acid is then determined. A candidate TMC is selected over an alternative TMC on the basis of the candidate TMC having a higher specificity for cleaving the elected regulatory element in comparison to cleaving the control nucleic acid, relative to the alternative TMC. This method can be carried out in vitro, or alternatively in situ, or in vivo, provided that an mRNA containing the elected regulatory element and an mRNA containing the control nucleic acid(s) are contained by the cell and the non-human animal respectively. A selected candidate TMC can then be further selected for with another in vitro, in situ or in vivo method of the present invention. Almost any nucleic acid or collection of nucleic acids may be used as the control nucleic acid including a polyA$^+$ RNA, collections thereof, a plasmid DNA, collections thereof and the like.

In one particular embodiment a TMC is selected by a process comprising contacting a TMC with a ferritin iron response element (IRE) and a transferrin receptor IRE. The relative specificity of the TMC to cleave the ferritin IRE relative to the transferrin receptor IRE is determined in vitro and a candidate TMC that cleaves the ferritin IRE with specificity relative to the transferrin receptor IRE is selected. The specificity of the candidate TMC is then enhanced by varying the organic ligand and determining its relative specificity for the ferritin IRE relative to the transferrin receptor IRE. The variation of the organic ligand is based, at least in part, on corresponding structural studies of the ferritin IRE and an enhanced TMC is selected for enhanced specificity for the ferritin IRE. The relative specificity of the enhanced TMC to cleave an mRNA comprising the ferritin IRE relative to a collection of nucleic acids selected from of a collection of polyA$^+$ RNAs and a collection of plasmid DNAs is determined in vitro. An elected TMC is selected on the basis of its ability to cleave the ferritin IRE while causing a minimum of cleavage of the collection of nucleic acids. The elected TMC is then contacted with a eukaryotic cell containing an mRNA comprising the ferritin IRE. The relative specificity of the elected TMC to cleave the ferritin IRE and thereby alter the rate of ferritin synthesis, relative to its disruption of a normal cellular function in the eukaryotic cell is then determined. A chosen TMC is selected on the basis of its ability to cleave the ferritin IRE while causing a minimum disruption of a normal cellular function in the eukaryotic cell as defined above. The chosen TMC is next administered to a non-human animal containing an mRNA comprising the ferritin IRE. Finally the relative specificity of the chosen TMC to cleave the ferritin IRE and thereby alter the rate of ferritin synthesis relative to its disruption of normal cellular functions in the non-human animal is determined. A selected TMC is selected on the basis of its ability to cleave the ferritin IRE and thereby increase ferritin synthesis while causing a minimum disruption of a normal cellular function in the non-human animal.

In one such particular embodiment, the degree of disruption of a normal cellular function is determined by evaluating a property of the eukaryotic cell such as determining cellular poly $A^+$ integrity. In another embodiment the degree of disruption of a normal cellular function is determined by determining the cellular DNA integrity. In a further embodiment, the degree of disruption of a normal cellular function is determined by quantifying cellular protein synthesis. In still another embodiment, the degree of disruption of a normal cellular function is determined by quantifying cell growth. In yet another embodiment, the degree of disruption of a normal cellular function is determined by evaluating cell viability as determined as a percentage of trypan blue exclusion. In an still an alternative embodiment two or more of these determinations are performed.

The present invention also provides methods of selecting a candidate TMC that include varying the organic ligand of the TMC, and thereby modifying the TMC. The modified TMC may then be further selected for by an in vitro method of the present invention, or alternatively, by an in situ or an in vivo method of the present invention. The modifying of the organic ligand is preferably based on, at least in part, the corresponding structural studies of the elected regulatory element.

Another aspect of the present invention provides a method of selectively enriching for a collection of cDNAs that comprise a regulatory element that has a binding affinity for an elected TMC. One such method comprises incubating a collection of mRNAs with an elected TMC attached to a solid support matrix. The collection of mRNAs consists of at least one mRNA that comprises a regulatory element with a binding affinity for the elected TMC, and at least one mRNA that does not comprise a regulatory element with a binding affinity for the elected TMC. mRNAs that do not bind the elected TMC are removed. The mRNAs that do bind the elected TMC are then eluted. Elution can be performed with a salt gradient, competing RNAs, or by other such methods well known in the art. The eluted mRNAs are then amplified by RT-PCR, therein forming a collection of cognate cDNAs which are enriched for cDNAs that comprise a regulatory element with a binding affinity for the elected TMC. In a preferred embodiment of this type the TMC that is attached to the solid support is placed in a column prior to the elution step.

Another related embodiment comprises incubating a collection of mRNAs, anaerobically with an elected TMC which is attached to a solid support matrix. The collection of mRNAs consists of at least one mRNA that comprises a regulatory element with a binding affinity for the elected TMC, and at least one mRNA that does not comprise a regulatory element with a binding affinity for the elected TMC. The mRNAs that do not bind the elected TMC are removed under anaerobic conditions. The mRNAs that do bind the elected TMC are then eluted under anaerobic conditions. Elution can be performed anaerobically with a salt gradient, competing RNAs, or by other such methods well known in the art. The eluted mRNAs are then amplified by RT-PCR therein forming a collection of cDNAs enriched for cDNAs that comprise a regulatory element with a binding affinity for the elected TMC. In a preferred embodiment of this type the TMC that is attached to the solid support is placed in a column prior to the elution step.

Another aspect of the present invention provides a method of treating an animal subject experiencing an iron overload, e.g., having elevated levels of iron, comprising administering a therapeutic amount of a TMC that has been selected by an in vivo method of the present invention. The TMC increases cellular ferritin synthesis by cleaving the ferritin IRE, thereby detoxifying the iron through ferritin binding the iron. The ferritin IRE functions as a negative regulatory site for the translation of the mRNA encoding ferritin, and the selected TMC selectively cleaves the ferritin IRE, thereby impairing its function as a negative regulatory site which results in an increase in the concentration of cellular ferritin synthesis. Therefore the TMCs and related methods of selection thereof of the present invention may be used in the treatment of thalassemia, sickle cell anemia, and hemochromatosis.

Still another aspect of the present invention includes pharmaceutical preparations for treating an animal subject experiencing an iron overload, e.g., having elevated levels of iron. In one such embodiment, there is provided a pharmaceutical preparation for the treatment of animal subject having elevated levels of iron comprising a TMC that has been selected by an in vivo method of the present invention, along with a pharmaceutically acceptable carrier. Such pharmaceutical compositions may be used in the treatment of thalassemia, sickle cell anemia, and hemochromatosis.

These and other aspects of the present invention will be better appreciated by reference to the following drawings and Detailed Description.

2B depicts a competition titration between cold ferritin-IRE and labeled TFR-IRE for the IRP. The ratio indicated is the proportion of cold ferritin-IRE to $^{32}$P labeled-TfR-IRE, with the amount of ferritin-IRE increasing from an equal amount, i.e., 1:1, to a ten fold excess, i.e., 1:10, over the $^{32}$P labeled-TfR-IRE. The two control lanes, i.e., 0 ferritin-IRE, indicate no cold ferritin-IRE was added. The "-" IRP lane, indicates no IRP was added. Note the smaller amounts (66±6%) of TfR-IREc bound compared to ferritin IRE and the poorer competition by TfR IRE for IRP binding. The results are representative of four experiments.

Figure 3:
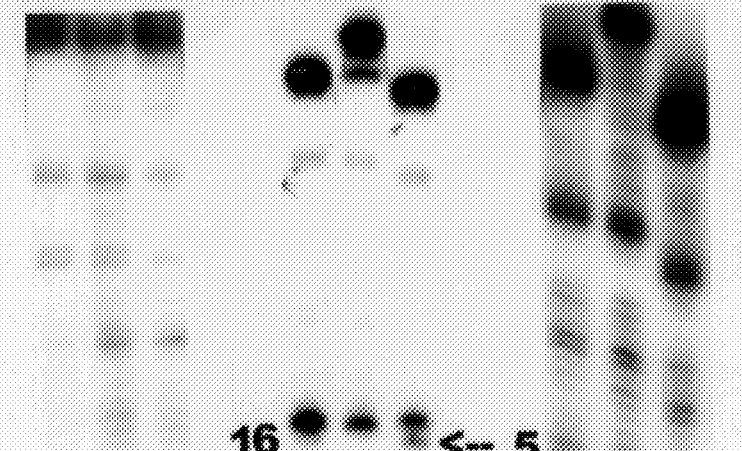
Figure 3:
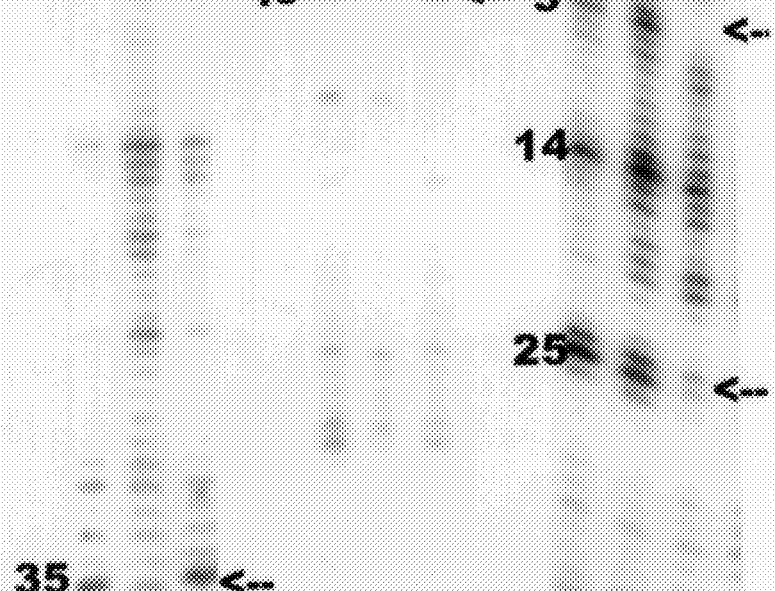

FIG. 3 depicts gels that visualize IRE sites cut by TMCs. Wild type (w.t.), mutated ferritin IREs were cut with TMCs. The figure depicts full-length, capped in vitro transcripts (n=1000 nt). FIG. 3A depicts the results with the TMC being Rh(phen)phi: lane 1,2,3 w.t, FL2, FL2R (triplet of base pairs restored in hextuple mutation). FIG. 3B depicts the results with the TMC being Ru(tpy)bpy: lane 1,2,3 w.t., IL 1, HL 1; selectivity of (tpy)bpy illustrated (by two hairpin loop mutations with changed reactivity in only IL-1. FIG. 3C depicts the results with the TMC being Cu(Phen)$_2$: lanes 1,2,3 w.t., HL 1, IL 1; reactivity of IL (G5,G25) is changed by deletion of U4/C6).

Figure 4A:
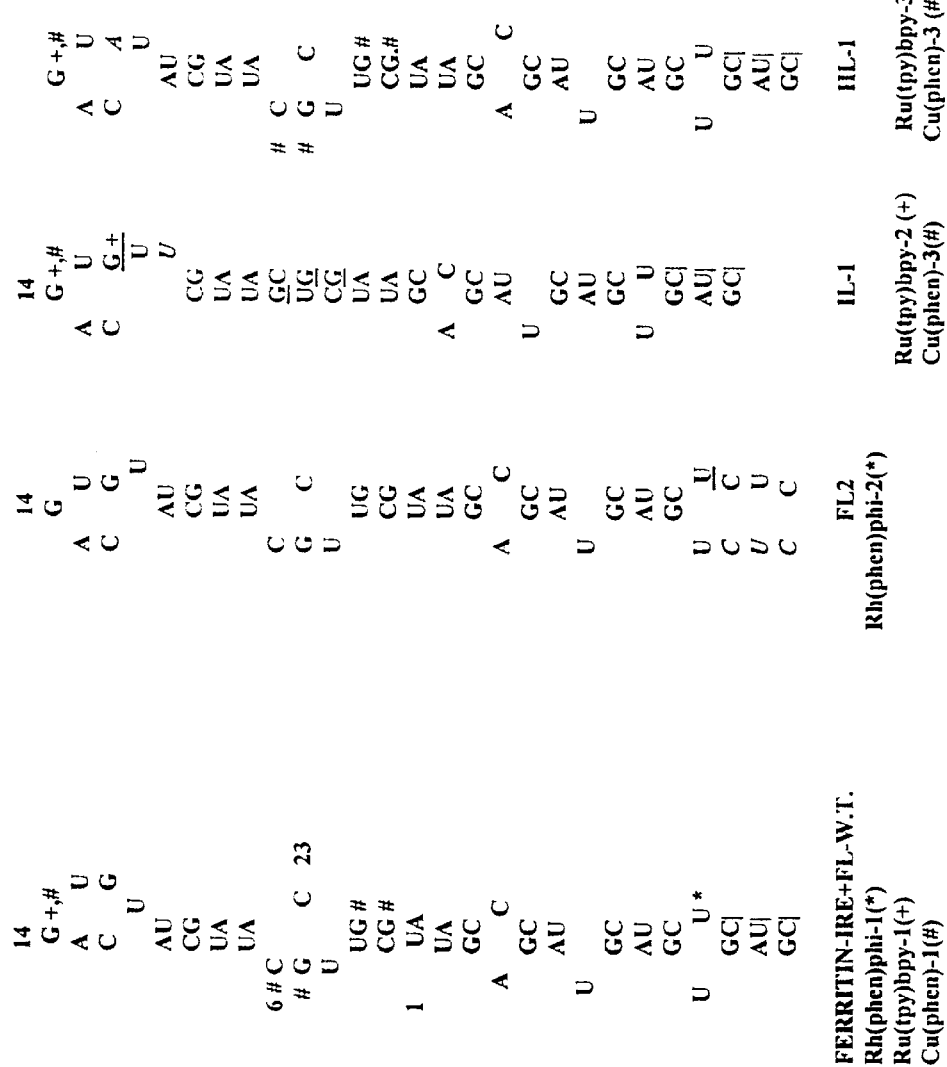
Figure 4B:
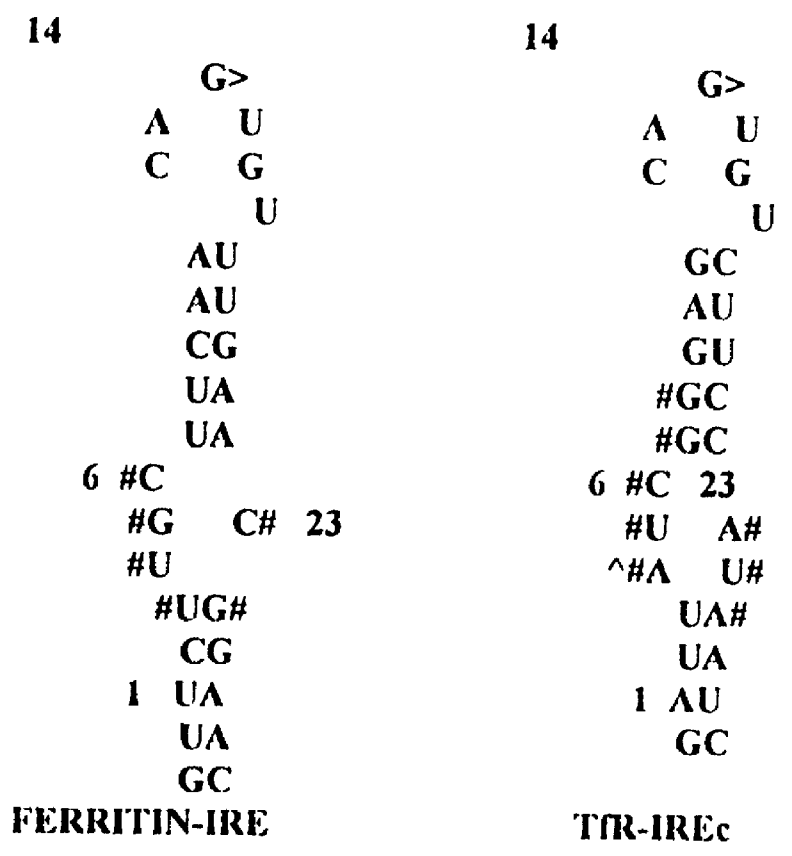

FIG. 4A shows the secondary structure predications of mutated and wild type ferritin IREs. Changed bases are italicized. Sites of altered TMC reactivity are underlined. FIG. 4B depicts similarities and differences in TMC reactivity for ferritin and TVR IREs. Cu(phen)$_2$ recognition of the IL is the same for the ferritin and TfR IREs (#), but Fe bleomycin recognizes a unique site in the TfR IRE (^=A at position 4). Some of the data are taken from Wang et al. [1990, supra]; Dix et al. [1993, supra]; and Thorp et al. [*Inorganic Chemistry*, 357/15/96: 2773–2779 (1990)].

Figure 5:
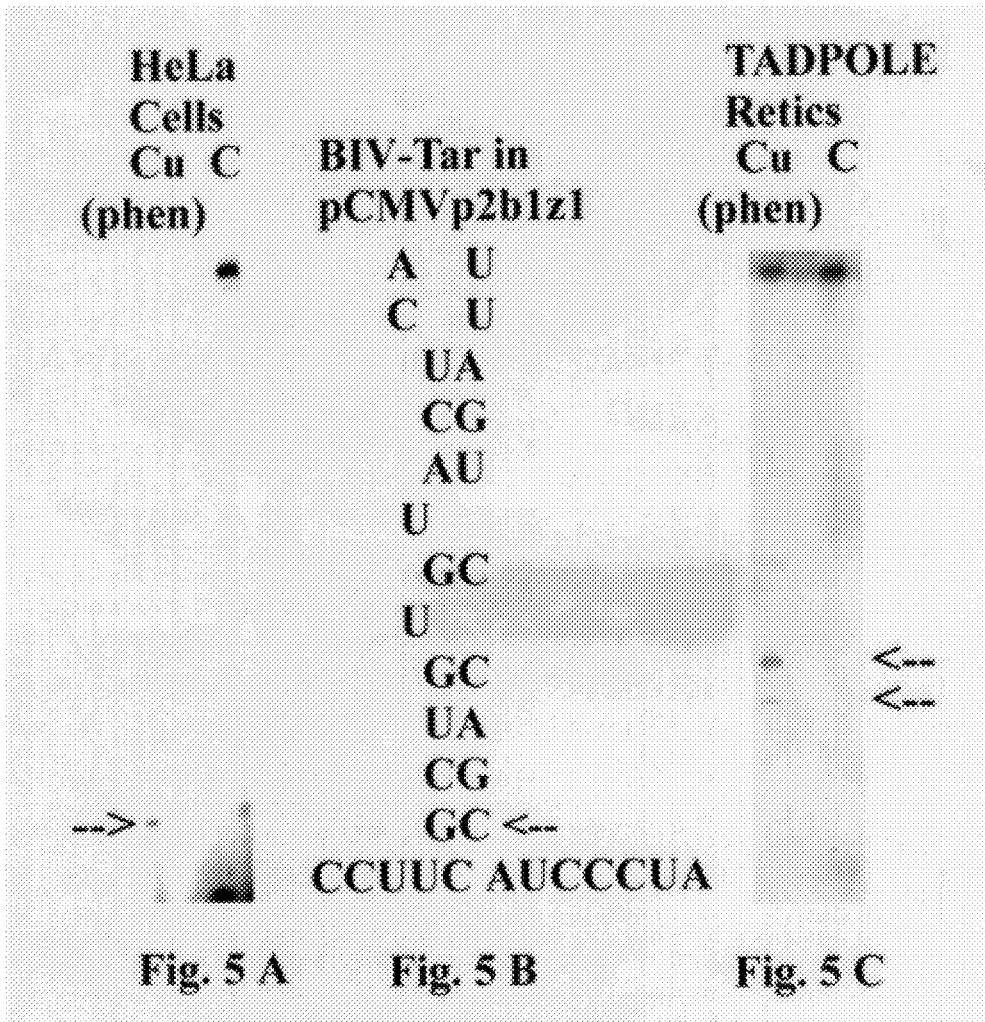

FIG. 5 depicts the cleavage of mRNA by Transition Metal Complexes (TMCs) in vivo, as visualized by gel electrophoresis. (Transfected HeLa cells or tadpole reticulocytes). Cu(phen)$_2$ was added to HeLa cells in Eagle's DMEM 10% FBS medium 24 or 48 hours after transfection with pCMVp2b1Z1, which contains a BIV tar sequence upstream from a β-gal reporter; transfection efficiency was 25–40%. Reticulocytes were collected at 40–50% maturity and incubated in Amphibian Ringer's solution with amino acids [Shull and Theil, *J. Biol. Chem.*, 257: 14187–14191 (1982)]. PolyA$^+$ RNA was isolated from the cells (Qiagen oligo-tex) and analyzed by primer extension; primers bound 20–40 nucleotides downstream from the region of interest [Wang et al., 1990, supra]. Cleavage sites were identified in the gel for the BIV-Tar mRNA in HeLa by calibration with dideoxysequencing cDNA reactions transcribed from the DNA. FIG. 5A depicts BIV-Tar in HeLa cells encoded in transfection vector pCMVp2b1Z1. FIG. 5B shows the secondary structure of the BIV-Tar element showing the Cu(phen)2 cleavage site. FIG. 5C depicts H- ferritin-IRE in tadpole reticulocytes in endogenous mRNA. The results are representative of three experiments for transfected HeLa cells, and one experiment for tadpole reticulocytes. Note the absence of full length BIV Tar mRNA in Cu(phen) treated HeLa cells. "C" denotes RNA analyzed from control cells. The arrows indicate in vivo cleavage sites with Cu(phen)$_2$.

DETAILED DESCRIPTION OF THE INVENTION

The present invention in its broadest embodiment, provides protocols and methodology for selecting and designing transition metal complexes (TMCs) that can modulate the translation of an mRNA by selectively cleaving a regulatory element of the mRNA. In a related aspect of the present invention, methods of identifying and characterizing mRNAs that contain regulatory elements that can be targeted by the TMCs of the present invention are provided. Such methods can be used in both in vitro studies to better characterize the regulation of particular mRNAs, and for treatments of diseases that involve the mRNA regulatory effect of a regulatory element.

Therefore, if appearing herein, the following terms shall have the definitions set out below As used herein, a "TMC" as used herein is a Transition Metal Complex that comprises an organic ligand and an oxidative metal. Examples of TMCs include Rh(PHEN)$_2$PHI$^{3+}$, Ru(TPY)(BPY)O$^{2+}$, Cu-(PHEN)$_2$OH$^{2+}$ or 1, 10-Phenanthroline-Cu, Ni(phen)$_2$$^{2+}$, and Fe-bleomycin .

As used herein a "protein footprint" encompasses the sites of an mRNA protected from being cleaved by a specific nuclease or a specific TMC, when the mRNA is bound to its corresponding binding protein.

As used herein "determining a cleavage activity" of the candidate TMC for the elected regulatory element involves a determination of the amount and/or rate of RNA cleavage at a specific site, including by indirect methods such as by determining the rate and/or amount of expression of protein encoded by the mRNA that is targeted for cleavage. Cleavage activity can be determined by any standard kinetic assay including by determining the amount and/or rate of labeled RNA that has been cleaved by a TMC; or the amount or rate of protein expressed that is encoded by the mRNA that is targeted for cleavage. Such reactions can be monitored by radioactive or fluorescent measurements and/or by gel electrophoresis as described below.

As used herein, "(phen)$_2$phi" represents bis (phenanthroline)(phenanthrene quinone diimine); "(tpy) bpy" represents (2,2',2'''-terpyridine)2,2'bipyridine; and "(phen)$_2$"represents 1,10- phenanthroline.

Thus the RNAs used in the present invention and/or proteins encoded by the mRNAs can be labeled; or alternatively the RNAs can be copied by reverse transcriptase using labeled primers. Suitable labels include radionucleotides, fluorescent moieties or a luminescent moieties. Such labels may be attached to the RNA or protein for example, e.g., a $^{32}$P labeled RNA, or alternatively, attached to binding partner to the RNA or protein, such as a labeled antibody to the protein. The TMCs of the present invention may also be suitably labeled with a radionucleotide. In the instance where a radioactive label, such as the isotopes $^3$H, $^{14}$C, $^{32}$P, and $^{35}$S are used, known currently available counting procedures may be utilized.

Specificity of Interactions of IREs with Transition Metal Complexes (TMCs) in vitro and in situ.

TMC cleavage of a regulatory element, can be initially examined in vitro, with a natural mRNA containing that regulatory element, using the polyA$^+$ fraction of a cell, for example, that preferably contains a significant amount of that mRNA. For example, in embryonic bullfrog tadpole red cells, ferritin mRNA makes up about 10% of the total mRNA of the cells [Shull and Theil, 1982, supra]. In such a case, a ferritin mRNA specific primer and reverse transcriptase can be used to synthesize a collection of cDNA fragments that correspond to the cleaved RNA fragments. Separation of the fragments can be performed by gel electrophoresis in an urea acrylamide gel, for example, which can be calibrated with a set of dideoxynucleotide fragments, [Wang et al., 1990, supra; Harrell et al., 1991, supra]. The initial use of natural mRNA creates a base line and assures that sites observed later in full length in vitro transcripts and oligomers corresponded to the natural mRNA [Dix et al., 1993, supra; Sierzputowska-Gracz et al., Nucl. Acids Res., 23: 145–152 (1995); Thorp et al., 1996, supra].

Significant amounts of a single species of mRNA can be produced in cultured mammalian cells by transfection with plasmids with very efficient promoters such as CMV. Other suitable promoters include but are not limited to, the SV40 early promoter region [Benoist and Chambon, Nature, 290: 304–310 (1981)], the promoter contained in the 3' long terminal repeat of Rous sarcoma virus [Yamamoto et al., Cell, 22: 787–797 (1980)], the herpes thymidine kinase promoter [Wagner et al., Proc. Natl. Acad. Sci. U.S.A., 78: 1441–1445 (1981)], the regulatory sequences of the metallothionein gene [Brinster et al., Nature, 296: 39–42 (1982)]; or the tac promoter [DeBoer et al., Proc. Natl. Acad. Sci. U.S.A., 80: 21–25 (1983)].

In the case of mRNA containing the ferritin-IRE, transfected HeLa cells can be selected because they are well characterized, easy to culture and display typical iron dependent regulation of ferritin expression [Cairo et al., Biochem. Biophys. Res. Comm., 133: 314–321 (1985)], indicating that the trans factors required for ferritin IRE dependent regulation are present in HeLa cells. Furthermore, in this case the ability to detect the target mRNA by primer extension analysis is possible both in cultured HeLa cells and in cell suspensions of reticulocytes from tadpoles.

$^{32}$P, fluorescent or luminescent primers can be selected to bind a chosen nucleotide sequence of the mRNA which is transcribed after transfection of HeLa cells with DNA of the plasmid; or alternatively the $^{32}$P, fluorescent or luminescent primers can be selected to bind to the endogenous mRNA of a cell that naturally contains the mRNA.

Cleavage of the target mRNA following the contacting of the cell with a TMC and incubating for a specified time, (as performed in the Example) can then be examined by gel electrophoresis for example. Following the incubation with the TMC, cellular integrity can be checked, e.g., determining if cell lysis has occurred and/or quantitating cellular damage by trypan blue exclusion, for example.

TMC targeting and analysis of ferritin mRNAs in mammalian cells.

In order expand the body capacity to store excess iron in conditions associated with transfusional iron overload or hemochromatosis by increasing ferritin synthesis "prophylactically", transition metal complexes can be developed to inactivate the ferritin IRE. The TMCs can cleave the ferritin IRE at specific sites in vitro (Table 1) and cleave a plasmid encoded mRNA, when tested with HeLa cells (FIG. 5). Cleavage will remove the cap but decapped ferritin mRNAs are stable and are translated in cell extracts. [Dickey et al., 1988, supra; Dix et al., 1993, supra]. Since plasmids encoding both H ferritin IRE+FL and L ferritin IRE+FL RNA are compared, the significance of conserved differences in FL sequence (FIG. 1; [Dix et al., 1993, supra]) are examined. L and H ferritin IRE+FL differ in the bases of the conserved triplet of base pairs in the FL (FIG. 1; [Dix et al., 1993, supra]) and in the composition of the IRE lower stem (Table 2 below; [Theil, 1994a, supra]).

TABLE 1

Results of Probing Ferritin- or TfR-IREs with Transition Metal Compleses (TMCs)

| TMC | TRE | Observation | Reference |
|---|---|---|---|
| Cu(phen)$_2$OH$^+$ (1,10-phenanthroline-Cu) | Ferritin | Multiple Mg-dependent conformations | Wang et al., 1990 |

TABLE 1-continued

Results of Probing Ferritin- or TfR-IREs with Transition Metal Compleses (TMCs)

| TMC | TRE | Observation | Reference |
|---|---|---|---|
| Cu(phen)$_2$OH$^+$ | Ferritin | Distortion in the helix at the IL$^a$ junction (mutation, sensitive) | Wang et al., 1990 |
| Cu(phen)$_2$OH$^-$ | TfRc$^a$ | Distortion in the helix; an IL not a "bulge"; | |
| Rh(phen)$_2$Phi$^{3+}$ | Ferritin mRNA | Distortion in FL helix at TBP$^a$; (mutation sensitive) | Thorp et al., 1996 |
| Fe-Bleomycin | Ferritin mRNA | Long range iteraction between TBP and IRE (mutation sensitive) | Dix et al., 1993 |
| Fe-Bleomycin | Ferritin mRNA | Distinct site at 3' HL/stem junction | Dix et al., 1993 |
| Fe-Bleomycin | TfRc$^a$ | Distinctive site near C6 at the "bulge" | |
| Ru(tpy)bpyO$^{2+}$ | Ferritin | Single site in entire IRE; in HL (mutation sensitive) | Thorp et al., 1996 |
| Fe-EDTA | Ferritin | IRP- "footprint" covers entire IRE | Harrell et al., 1991 |
| Fe-EDTA | Ferritin | IRE folding creates self-protection for upper and lower stems and parts of HL | Harrell et al., 1991 |

IL-internal loop, HL = hairpin loop, TfR-transferrin receptor; FL = ferritin specific, base paired IRE flanking region; TBP = conserved triplet of base pairs conserved in the FL of all 9 vertebrate ferritin IREs (Dix et al., 1993).

TABLE 2

Phylogenetic CONSERVATION within IRE Types Compared to VARIATION Among IRE Types

| IRE Type | Phylogentic Sequence Conservation % | Sequence Variation in Humans Rats Chicks (Human, Rat, Mouse, Rabbit, Chick, Frog$^a$) | | | Variation in G/C Base Pair Distribution | |
|---|---|---|---|---|---|---|
| | | % | % | % | Upper Stem | Lower Stem |
| mRNA Translation Regulator | | | | | | |
| Ferritin | 97 | 34 | — | — | 3 | 2–3 |
| eALAS | 97 | 36 | —$^a$ | —$^a$ | 3 | 2 |
| mRNA Stability Regulator | | | | | | |
| Transferrin receptor (TfR)-a | 99 | 100 | 100 | 100 | 2 | 0 |
| TFR-b | 96 | 56 | 58 | 44 | 3 | 0 |
| TFR-c | 98 | 59 | 60 | 63 | 3 | 1 |
| TFR-d | 96 | 74 | 70 | 65 | 3 | 1 |
| TFR-e | 99 | 67 | 67 | 70 | 3 | 0 |

$^a$Ferritin IREs: (Human-H,L; Rat-H,L; Mouse-H; Rabbit:L; Chick-H; Frog-H,H', TfR IREs: Human, rat chick; eALAs IREs: human, mouse. For the eALAS comparision to the TfR-IREs only the values for human could be determined with available sequence information.

In one particular embodiment the plasmid pCMVp2b1z1 can be used to insert the H ferritin IRE+FL and the L ferritin IRE+FL downstream from the CMV promoter and upstream from a reporter gene, e.g., β-gal. The pCMVp2b1z1 plasmid is constructed from Stratagene plasmid pBK-CMV, by insertion of a LacZ sequence between the Nhe I and Hind III sites and insertion of the BIV-tar sequence in the Bam H I site upstream from the LacZ gene. Deletion of the BIV tar sequence from pCMVp2b1z1 can be accomplished by EcoR1 and Nhe 1 digestion; the H ferritin IRE+FL or the L ferritin IRE+FL can then be inserted into the EcoR1 and Nhe 1 sites, upstream from the Lac Z sequence. The two IRE+FL sequences can be synthesized as two sets of oligonucleotide sequences containing the H ferritin or L ferritin IRE+FL (FIG. 1) with sequences corresponding to the "sticky ends" of the digested Nhe1 and EcoR1 sites at each end. The complementary oligonucleotides of each pair can be melted, annealed, ligated to the digested pCMVp2b1z1 vector, and transformed into HB101 for amplification. If needed, FL deletion constructs can be made with oligonucleotides containing just the H-ferritin IRE and the L-ferritin IRE (FIG. 1); all constructs can be sequenced.

Synthesis of ferritin IRE-specific Transition Metal Complexes (TCMs)

Synthesis of TMCs with enhanced speificity for the ferritin-IRE is based on the high specificity of ligand/RNA interactions in general (reviewed in Gold et al. [*Ann. Rev. Biochem.*, 64: 763–797 (1995)]), the small number of alternate IREs identified by SELEX [Henderson et al., *J. Biol. Chem.*, 269: 17481–14789 (1994); Butts et al., *Proc. Natl. Acad. Sci.*, 93: 4345–4349 (1996)], and the high specificity of ferritin-IRE/TMC interactions already observed [reviewed in Theil, *New J. of Chem.*, 18: 435–441 (1994b); see FIG. 3]. Phenanthroline, is a preferred organic ligand for three reasons: (1) a large amount of structural information exists; (2) three dimensional shape is rigid; and (3) changes in substitutents of phenanthroline are very sensitive probes of small changes in DNA conformation [Franz and O'Halloran, *Biochemistry*, 29: 4747–4751 (1990)]. Cu-phen derivatives are prepared that have increased specificity for the ferritin IREs relative to the transferrin receptor IREs and other background DNA and RNA. The approach involves synthesis of a family of substituted Cu-phen complexes according to the following reaction scheme:

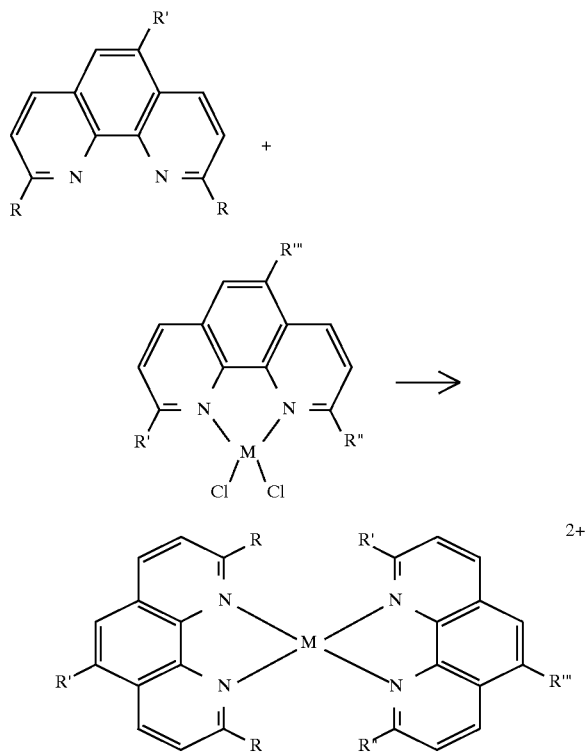

where R and R"=H, Me, Ph; R' and R'"=H, Ph. The complex where R=R"=Me does not cleave nucleic acids [Sigman, *Acc. Chem. Res.*, 19: 180 (1986)]; however, the complexes where R=H and R"=Me or Ph are active as cleavage agents.

Complexes are screened initially for cleavage activity. The selection of methyl and phenyl for R allows the role of the cationic charge and conformation of the metal center to be assessed. Increased tetrahedral geometry can be achieved as the size/shape of the R-group is increased. The negative charge of the phosphate of the RNA has a lessor effect on the cationic charge of the ligand. In a previous study, the addition of phenyl group at R' increased specificity enough to detect Hg-dependent alterations in the MerR-repressor complex that controls detoxification of mercury in *E. coli* [Frantz and O'Halloran, 1990, supra]. The TMCs are screened for specificity in cleavage reactions of ferritin IREs as described below.

Purified (Qiagen) DNA can be used to transfect HeLa cells. Cells can be cultured in DMEM medium (10% fetal bovine serum) and transfected with lipofectin (GIBCO), using OPTI MEM (GIBCO) medium and the conditions recommended by the supplier. The mRNA that is encoded in the plasmid template, can be isolated using Qiagen Oligotex, for example, and cleavage sites are analyzed by primer extension analysis (FIG. 5).

Analysis of IRE sites cleaved by TMCs in vitro and in vivo.

As new TMCs are synthesized, the specificity can be tested first in vitro, by comparing the reactivity of H- and L-ferritin IRE+FLs with a TFR-IRE. The most promising TMCs in terms of ferritin IRE specificity can then be tested in vivo using cultured Hela cells. TMCs which cleave the ferritin IRE in HeLa cells can then be tested in mice.

Such a TMC can be administered to the mice by injection, for example. Following the administration of the TMC and an appropriate incubation time, e.g., (6 to 24 hours) relevant tissues can be collected from the mice. Cells and/or RNA are then isolated from the collected tissues and are analyzed as described above for the HeLa cells. Alterations in the amount and/or rate of expression of mRNA containing the regulatory element due to the cleavage activity of the TMC can be determined by constructing the mRNA such that it encodes a marker protein, such as β-galactosdase.

The results described in the Example, provide insight about regions of similarity and differences in the 3-dimensional structure of H- and L-ferritin IREs and TfR-IREs. Such information is important for understanding the structural basis of the differences in IRE function of ferritin IREs (regulation of translation) and TfR IREs (regulation of mRNA stability). The results can also provide basic information about nucleic acid targets for TMC radical chemistry in vivo.

To determine which of the newly synthesized compounds has increased specificity for the ferritin IRE, reactivity with RNAs and DNA can be analyzed and compared in vitro. Five types of RNA to be examined first are H and L ferritin IRE+FL (55 nt), transferrin receptor IREc (29 nt), full-length ferritin mRNA (n=1000 nucleotides), HeLa polyA+ and DNA (pBR322).

TMC specificity for ferritin IREs compared to TfRr IREs.

Identification of TMCs with enhanced specificity for the ferritin IRE as compared to the TFR-IRE, for example can be sought among new phenanthroline derivatives synthesized using specific design methods. Such studies are partially based on the finding that Fe bleomycin distinguishes between the ferritin IRE and the TfR IREc (FIG. 4B). Moreover, in analyzing subtle changes in DNA structure, the addition of a bulky side chain to $Cu(phen)_2^{2+}$ changed specificity significantly [Frantz and O'Halloran, 1990, supra]. Finally, a $10^3$-fold change in ligand binding occurred with the addition of a methyl group to an RNA recognition site [Jenison et al., *Science*, 263: 1425–1429 (1994)].

Figure 1:
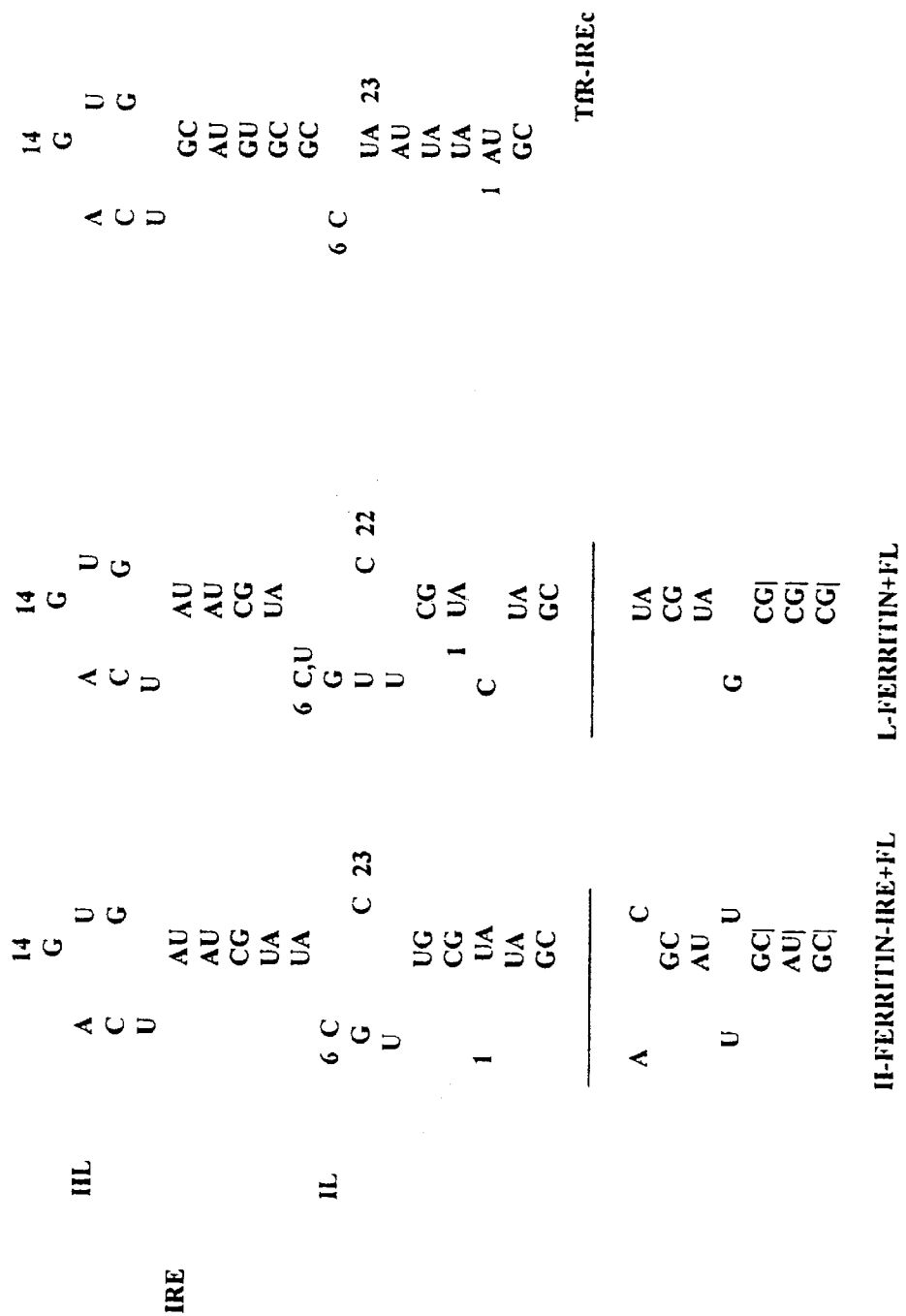
FIG. 1 shows the predicted Secondary Structure of H-Ferritin-IRE, L-Ferritin-IRE and a Transferrin Receptor IRE. Note the identity of the hairpin loop in all IREs. The predicted interruption of the base pairs in the stem is an internal loop (IL) in the ferritin IRE and a single nucleotide bulge in TfR-IREs. (In solution, the TFR-IRE has a distortion in the stem as large as the IL in the ferritin-IRE based on chemical reactivity (preliminary results). Base paired flanking regions (FL) are found in all vertebrate ferritin mRNAs; a triplet of base pairs (TBP) conserved through compensatory mutation, and shown by vertical lines in the figure, modulate ferritin mRNA regulation [Dix et al., *J. Mol. Biol.*, 231: 230–240 (1993)].

Initially, TMC specificity is analyzed by comparing the reactivity of H ferritin IRE+FL, L-ferritin IRE+FL and TfRc-IRE (FIG. 1). Cleavage reactions, electrophoretic separation of cleaved RNA fragments, RNA synthesis, and end labelling of shorter RNAs can follow procedures previously used [Wang et al., 1990, supra; Harrell et al., 1991, supra; Dix et al., 1993, supra; Thorp et al., 1996, supra]. TMC specificity for ferritin IREs compared to full length ferritin mRNA, polyA+ RNA and DNA.

TMCs with enhanced specificity for the ferritin IRE+FL, identified in comparisons with TfR IREs, can be further examined by measuring cleavage of full length H ferritin mRNA (n=1000), polyA+RNA and DNA. Ferritin mRNA cleavage can be measured by primer extension using labeled primers that bind to positions: +250, +500, +750, or the poly A tail, which is part of the mRNA encoded in plasmid BFH 1DV [Dix et al., 1992, supra]. Cellular mRNA reactivity with selected TMCs can be determined as the size and relative amount of fragments of HeLa polyA$^+$ RNA (Clontech) produced using primer extension analysis with oligo dT as the primer. DNA reactivity with the selected TMCs can be explored using pBR322 DNA by measuring the loss of supercoiled DNA using electrophoresis in 1% agarose gels with ethidium bromide staining.

Cells, such as transfected HeLa cells described above, can be treated with selected TMCs that show high ferritin-IRE specificity in vitro; the general treatment conditions are exemplified in the FIG. 5, but a range of concentrations are tested for each TMC analyzed. Cell viability can be examined by trypan blue exclusion, for example. Cells can be washed, frozen in liquid nitrogen and used for isolation of polyA$^+$ RNA. Qiagen reagents for guanidine isothiocyanate extraction, and "spin column" oligo-dT affinity chromatography (oligo-tex) can be used as described in the Example. IRE-cleavage sites can be analyzed by primer extension analysis, using specifically labelled primers as previously described [Wang et al., 1990, supra; Thorp et al., 1996, supra; FIG. 5] with $^{32}$P-labelled primers annealed downstream from the IRE+FL site. Adequate amounts of specific mRNA could be obtained for sequencing from 2–3 wells of the HeLa cell culture (FIG. 3). Dideoxy sequencing reactions using the same primer and plasmid DNA can be used to calibrate the gel [Wang et al., 1990, supra].

IRE function can be measured as iron dependent increases in β-gal expression following culture of the transfected cells with ferric ammonium citrate 100 μg/ml for 16 h [Iwai et al., EMBO J., 14: 5350–5367 (1995)]. Iron can be added 24 hours following transfection. TMCs can be tested in cells both with and without the iron treatment, at different TMC concentrations based on in vitro studies described above. If the TMCs are effective at inactivating the IRE+FL, β-gal expression in TMC treated control cells should be increased and may even exceed that in iron treated cells, without TMC exposure.

The effect of selected TMCs for ferritin IREs on polyA$^+$ RNA/DNA integrity, protein synthesis, and cell viability can be assessed in control and TMC-treated cells. PolyA$^+$ RNA integrity can be analyzed by using primer extension analysis as described above, with $^{32}$P-oligo-dT to assess the integrity of the ~400 nucleotides upstream from the polyA$^+$ tail. Northern blotting could also be used as previously described [Ragland et al., J. Biol. Chem., 263: 18339–18344 (1990)] to assess major changes in the size distribution of polyA$^+$-RNA, but it is unlikely to be as sensitive as the primer extension analysis. DNA integrity can be analyzed by analyzing relaxation of supercoiled plasmid DNA (pBR322), measuring 1% agarose gels with ethidium bromide staining. Protein synthesis can be measured as $^{35}$S incorporation into TCA precipitable protein from cells cultured with and without TMCs. Cell viability can be measured as % trypan blue exclusion. With more specific TMCs, cell viability should increase; with Cu(phen)$_2$OH$^{2+}$ (1,10-phenanthroline-Cu), trypan blue exclusion by HeLa cells decreased from 95% to 50% (in Example, below).

When the ferritin-IRE-specific TMCs are identified, the effects on growth can also be examined in cultures that are only 50% confluent at the time of TMC treatment (full confluency is reached in the cultures from which mRNA isolation was planned). After exposure to TMC for a time equivalent to that for TMC cleavage, the TMC-containing medium can be replaced with fresh medium Growth (cell number), viability (trypan blue exclusion) and the marker protein, e.g., β-gal and/or ferritin expression can be monitored.

Intracellular Distribution of TMCs.

Cell uptake and the intramolecular distribution of the TMCs can be determined for TMCs with enhanced ferritin IRE specificity, as identified in the procedures describe above. Labelled TMCs can be synthesized, for example using radioactive $^{14}$C. A limited number of TMCs are tested at a time, (for example the parent Cu(phen)$_2$, and two or three other related TMCs that have been modified as described above). After incubation of the TMC with cells under the same conditions used in the cleavage reactions, the cells can be harvested, washed (e.g., phosphate-buffered saline), and in lysed hypotonic sucrose 0.125 M [Wolff, In Methods in Cell Biology, DM Prescott (ed.), pp. 85–104, p. 99 (1975)]. Cell fractions can be obtained by differential sedimentation. Such fractions obtained can be: nuclei (1000×g, 8 minutes), mitochondria/lysosomes (20,000×g, 20 minutes), ribosomes and polyribosomes (100,000×g, 2 hours) and the soluble fraction (postribosomal supernatant). Measurement of radioactivity can be made for washed cells, culture supernatant solution, and cellular fractions, using tissue solubilizer and liquid scintillation counting [e.g. Dix et al., 1992, supra].

The effects of IRE specific Transition Metal Complexes (TMCs) on ferritin IRE regulated expression in mammalian cells.

Effect of TMCs on ferritin IRE regulated expression.

The level of TMC-produced hyperferrintinemia is compared to iron induction. Initial tests of IRE function can use the β-gal reporter, transiently transfected into HeLa cells in the pCMV IRE+FL LacZ constructs for the H and for the L ferritin IRE+FLs (FIG. 1). IRE function can be determined using the β-galactosidase reporter protein as described above. If differences are observed between H and L ferritin IRE+FL dependent expression, the contribution of the FL to regulation can be examined using constructs prepared without the FL as described above.

To confirm the inactivation of the IRE and the accumulation of IRE controlled protein in TMC treated cells, transient HeLa cells transfected with a plasmid encoding frog ferritin under the control of the IRE and the CMV promoter, can be analyzed for ferritin accumulation. Previous observations show that genetic inactivation of the IRE by spontaneous mutation of the L-ferritin IRE in the Verona mutation caused ferritin accumulation [L-hyperferritinemia [Girelli et al., 1995a, supra; Girelli et al., 1995b, supra]. Ferritin accumulation in treated HeLa cells (iron or TMCs) can be analyzed using western blotting with antibodies for frog ferritin; the methods to be used with frog ferritin antibodies and western blotting have been described previously [Shull and Theil, 1982, supra; Ragland and Theil, Plant Mol. Biol., 21: 555–560 (1993)]. [Note that frog ferritin antibodies do not react with human HeLa cell ferritin.] The ferritin encoding plasmids can be constructed by inserting the bullfrog H ferritin coding sequence from (pJD5F12, Didsbury et al., 1986) into pCMV H ferritin IRE+FL vector and the L chain ferritin coding sequence (pJD1D8, Dickey et al., *J. Biol. Chem.*, 262: 7901–7907 (1987)) into the pCMV L ferritin IRE+FL vector. If differences are observed in the IRE dependent regulation by iron for H- and L-ferritin IRE+FLs, the coding regions can be inserted into the pCMV IRE vectors which lack the FL to determine the role of the specific features in the H and L ferritin IRE flanking regions.

Identification and characterization of other mRNAs targeted by Transition Metal Complexes (TMCs).

The TMCs first used to probe the ferritin mRNA structure [Theil, 1994b, supra; Thorp et al., 1996, supra] can recognize 3-dimensional (3D) structures in other mRNAs, since the TMCs also cleave distinctive 3D structures in the t-RNA model [Carter et al., *Proc. Natl. Acad. Sci. U.S.A.*, 87: 9373–9377 (1990); Chow et al., *Biochemistry*, 31: 3534–3532; Murakawa et al., *Nucl. Acidss Res.*, 17: 5393–5395 (1989)]. Affinity chromatography with such a TMC should enrich cellular mRNAs with specific 3D structures. Amplification of the selected mRNAs, cloning and sequencing can characterize and possibly identify mRNAs with specific 3D structure recognize by the TMC.

The general strategy used to identify new mRNA targets for TMCs, described in detail below, is selective enrichment (SELEX) [Tuerk and Gold, *Science*, 249: 505–510 (1990); Gold and Turerk, U.S. Pat. No. 5,595,877 (1997); Gold and Turerk, U.S. Pat. No. 5,503,978 (1996); Gold and Turerk, U.S. Pat. No. 5,475,096 (1995); Gold and Turerk, U.S. Pat. No. 5,270,163 (1993); and Gold and Ringquist, U.S. Pat. No. 5,567,588 (1996), all of which are incorporated by reference in their entireties], using polyA$^+$ mRNAs from HeLa cells and an affinity matrix with noncleaving Ni(phen)$_2{}^{2+}$ [or Cu(phen)$_2{}^{2+}$ in the absence of oxygen]. A $^{32}$P-labelled full length transcript of the frog H-ferritin transcript (approximately 1000 nts), can be used to develop binding/elution conditions. Ligation of a T7 polymerase promoter sequence to mRNA [Kiss-Lazlo et al., *Cell*, 85: 1077–1088 (1996)] selected in the first round, and amplification using primers containing restriction enzyme sites can facilitate the necessary transcriptions for subsequent selective enrichment and cloning. Transcripts from pooled, cloned plasmids can be analyzed for reactivity with Cu(phen)$_2{}^{2+}$; individual plasmids used to make the pools with reactive sites can be characterized for DNA sequence, matches to known DNA sequences, and sequences around the TMC site in the RNA. PolyA$^+$ RNA from other human cell types (e.g. human liver, and bone marrow polyA$^+$ RNA purchased from Clontech) also can be analyzed.

Figure 2A:
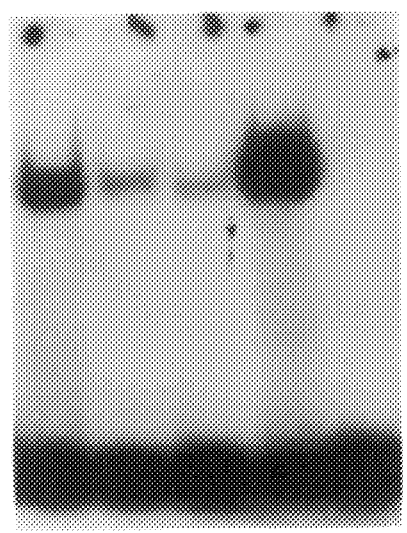
FIG. 2A depicts a competition titration between cold TFR-IRE and labeled ferritin-IRE for the IRP. The ratio indicated is the proportion of cold TFR-IRE to $^{32}P$ labeled-ferritin-IRE, with the amount of TFR-IRE increasing from an equal amount, i.e., 1:1, to a ten fold excess (i.e., 1:10) over the $^{32}P$ labeled-ferritin-IRE. The two control lanes, i.e., 0 TFR-IRE, indicate no cold TFR-IRE was added. In the "-" IRP lane, no IRP was added. FIG.
Figure 2B:
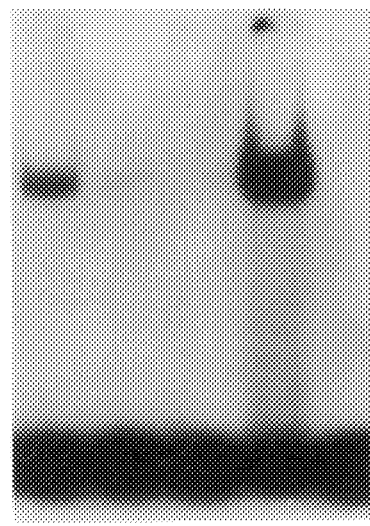
FIG. 2 shows the results of a gel-shift assay comparing the binding of the ferritin IRE and the TfR IREc to the IRP. IRP is an mRNA specific regulatory protein that binds IREs. The mRNA/protein ratio was 1:20.

The results can identify other mRNAs, particularly those involved in disease which have a 3D structure that could be futures targets for TMCs in vivo. In addition, Metal(phen)$_2{}^{2+}$ recognition sites in cellular mRNAs can be further characterized, indicating for example, whether other mRNAs with AU-rich stability elements are recognized by TMCs as are the AU-rich IREs in the TFR-RNA (FIG. 2). Preparation of the binding matrix (described in detail below).

Phen (1,10-phenanthroline) is used to exemplify a TMC for screening other mRNAs with 3D structures recognized by TMCs. The structure of Phen (1,10-phenanthroline) is rigid and the properties are extensively studied. Ni substitution for Cu in the (phen)$_2$ complex can make a TMC which should be unable to cleave mRNA on the affinity matrix, but with the same ligand shape as with the Cu form. In the unlikely event that the Ni(phen)$_2$ complex does cleave RNA when bound to the column (revealed by the development studies with $^{32}$P-ferritin mRNA), the columns can be run in the absence of oxygen, using the Cu(phen)$_2$ complexes.

Development of Binding and elution conditions.

The initial test of binding can use the conditions of the RNA cleavage reactions [Wang et al., 1990, supra]: 25 mM Hepes•Na, pH 7.0, 50 mM KCl and RNAse inhibitor. RNAs, heated to 65° for 5 minutes followed by slow cooling can be applied to the matrix, followed by washing with the Tris/KCl buffer and elution with 90 $\mu$M Ni (2,9-dimethy-phen)$_2$ or in 25 mM Tris, pH 7. The test RNA can be a $^{32}$P-transcript of full-length ferritin mRNA (from p1DV-[Dix et al., 1992, supra]). Measurement of radioactivity in the wash (25 mM Tris, 25 mM KCl) and eluant can analyze effectiveness of binding and elution. If necessary, the potassium chloride concentration can be varied to improve binding and/or elution. MgCl$_2$ may be introduced into the solution [Jenison et al., 1994, supra], although this usually is unnecessary for full-length mRNAs [Wang et al., 1990, supra]. When high efficiency of binding and elution of the ferritin mRNA is achieved, HeLa cell polyA$^+$ RNA can be bound and eluted, amplified and transcribed for selective enrichment.

Amplification, transcription and selective enrichment.

Each round of RNA can be converted to cDNA with reverse transcriptase using an oligo-dT primer [Didsbury et al., *J. Biol. Chem.*, 261: 949–955 (1986)], amplified by PCR and RNA synthesized by in vitro transcription. A T7 polymerase promoter can be introduced into the RNAs by ligation of the promoter sequence [Kiss-Lazlo et al., 1996, supra].

Amplification.

mRNAs isolated from the first round of selection can be ligated to a 5'end-phosphorylated oligoribonucleotide encoding a Bam H1 site and a T7 polymerase promoter site (n=17 nucleotides) using T4 RNA ligase as described by Kiss-Lazlo et al. [1996, supra]. The modified RNAs can be used as a template for cDNA synthesis, with oligo dT as the primer [Didsbury et al., 1986, supra]. Polymerase chain reaction using Pfu polymerase can amplify the cDNAs using primers containing the Bam-H1+T7 polymerase initiator site complement (left) or Sma I +oligo-dT (right). Such PCR methodology was exemplified first in Waldo et al. [*Science*, 259: 796–798 (1993)] where PCR generated the DNA inserts encoding ferritin subunits for protein expression.

Transcription.

PCR amplified DNA can be transcribed with T7 polymerase to generate the RNA sequences for the next round of selection. Transcription reactions can be followed as previously described [Dix et al., 1992, supra; Sierzputowska-Gracz et al., 1995, supra].

Selective enrichment.

RNA from each round can be bound to the Ni-phen$_2$-matrix. The percentage of total RNA eluted with the TMC can be monitored. As enrichment proceeds, the percentage can increase from 0.05% to >60% [Jenison et al., 1994, supra]. 5–8 rounds of selection is a likely range to anticipate, based on previous experiments [Jenison et al., 1994, supra; Methot et al., RNA, 2: 38–50 (1996)].

Cloning and analysis of sequences reacting with Cu(phen)$_2$OH$^+$(1,10-phenanthroline-Cu).

Cloning, after the last round of selection can use cDNA from the RNA, amplified by PCR with reverse transcriptase, as described above and cloned into the BamH1 and Sma1 sites of pBluescript, with *E. coli* XL-1 MRE' as the host. Clones with plasmids can be pooled in groups of ten, plasmid DNA isolated and the RNA synthesized using $^{32}$P-ATP as one of substrates. Methods for transformation, plasmid isolation and transcription have been described [Dickey et al., 1987, supra; Dix et al., 1992, supra]. RNA pools can be examined for strong cleavage sites with Cu(phen)$_2$ and analyzed in denaturing gels as previously described [Wang et al., 1990, supra]. Identification of individual plasmids encoding RNA with cleavage sites can be determined by examining the reactivity with Cu(phen)$_2$ of transcripts of the individual plasmids which formed the pool.

Characterization of plasmids encoding mRNAs that react strongly with Cu(phen)$_2$ can include DNA sequencing [Thorp et al., 1996, supra], attempts to match the sequences with known human DNA sequences in Genbank and determination of the sequence around the Cu(phen)$_2$ reactive site by reverse transcription of cleaved RNA, using $^{32}$P-primers deduced from DNA sequencing; dideoxy sequencing of the uncleaved RNA using reverse transcriptase, can provide a set of cDNAs to calibrate the gel and the location of the cut site(s) as described previously [Wang et al., 1990, supra].

Administration

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

According to the present invention, a therapeutic composition comprising a TMC of the invention may be introduced parenterally, transmucosally, e.g., orally, nasally, or rectally, or transdermally. Preferably, administration is oral.

In another embodiment, the therapeutic compound can be delivered in a vesicle, in particular a liposome [see Langer, *Science* 249: 1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.].

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

In another embodiment, the therapeutic compound can be delivered in a vesicle, in particular a liposome [see Langer, *Science* 249: 1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.].

In yet another embodiment, the therapeutic compound can be delivered in a controlled release system. For example, a TMC of the present invention may be administered using intravenous infusion, an implantable osmotic pump, a transdermal patch, liposomes, or other modes of administration. In one embodiment, a pump may be used [see Langer, supra; Sefton, *CRC Crit. Ref Biomed. Eng.* 14: 201 (1987); Buchwald et al., *Surgery* 88: 507 (1980); Saudek et al., *N. Engl. J. Med.* 321: 574 (1989)]. In another embodiment, polymeric materials can be used [see *Medical Applications of Controlled Release*, Langer and Wise (eds.), CRC Press: Boca Raton, Fla. (1974); *Controlled Drug Bioavailabilty, Drug Product Design and Performance*, Smolen and Ball (eds.), Wiley: New York (1984); Ranger and Peppas, *J. Macromol. Sci. Rev. Macromol. Chem.* 23: 61 (1983); see also Levy et al., *Science* 228: 190 (1985); During et al., *Ann. Neurol.* 25: 351 (1989); Howard et al., *J. Neurosurg.* 71: 105 (1989)].

Other controlled release systems are discussed in the review by Langer [*Science* 249: 1527–1533 (1990)].

As can be readily appreciated by one of ordinary skill in the art, the pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects for veterinary medical use, and in research animals, such as mice, rats, rabbits, goats, sheep, pigs, dogs, cats, etc. In a preferred embodiment, the subject animal is a human.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Selecting transition metal complexes which selectively cleave the ferritin iron responsive element Introduction Transfusional iron overload can limit effective management of diseases such as thalassemia and sickle cell anemia. Environmental iron overload causes tissue damage in hemochromatosis. Thus, the regulation of the cellular concentration of iron is a crucial factor in both the prevention and treatment of iron-related pathologies.

Under normal conditions ferritin concentrates iron early in cell differentiation to the levels needed ($\sim 10^{-7}$M). Ferritin overcomes the low solubility of the free ferric ion ($\sim 10^{-18}$M) by concentrating iron in a solid mineral, ~8 nm in diameter, at the center of the protein; ferritin is the only protein known which directs the phase transition of a metal ion in solution to a solid phase. In specialized cells, ferritin has additional, tissue-specific functions. Examples of specific function include rapid recycling of red cell iron though ferritin in erythrophagocytic macrophages and the long-term storage of iron for the entire organism in ferritin of hepatocytes. Cell specific differences occur in ferritin mRNA concentration and subunit (H and L) composition that are set during differentiation. The tissue-specific differences in ferritin structure likely relate to the tissue-specific functions [reviewed in Munro, *J. Cell. Biochem.*, 44: 107–115 (1990); Theil, *Ann. Rev. Biochem.*, 56: 289–315 (1987); Waldo and Theil, in *Comprehensive Supramolecular Chemistry*, Suslick KS (ed.), Vol. 5, Pergamon Press, Elsevier, Oxford, pp. 65–90 (1996)]. When iron is in excess of cellular or body need, or during inflammation and infection, stable ferritin mRNAs are derepressed. The stable ferritin mRNA is translated and ferritin is synthesized in larger amounts to detoxify the excess iron. Studies of the post-transcriptional regulation of ferritin, as well as of the transferrin receptor-IRE and erythroid aminolevulinate synthetase (eALAS-IRE) have been identified and demonstrate the role of the conserved, noncoding regulatory element, the IRE, in controlling the synthesis of the proteins encoded in the mRNAs [Klausner et al., 1993, supra; Theil, 1990, supra; Theil, 1994a, supra; Leibold and Guo, 1992, supra; Hentze, 1995, supra].

One strategy for enhancing ferritin synthesis in vivo is to specifically cleave the ferritin IRE in cells using TMCs. Decapped ferritin mRNA is both functional (i.e. it expresses ferritin) and is stable [Dickey et al., 1988, supra; Dix et al., 1992, supra]. Increasing ferritin synthesis in transfusional iron overload or hemochromatosis, through the development of TMC-based drugs to inactivate the IRE, could improve management of the diseases. The principle that "prophylactic" synthesis of ferritin can be advantageous was illustrated in cultured endothelial cells where accumulated ferritin protected the cells against oxygen toxicity [Balla et al., 1992, supra]. Hyperferritinemia itself is relatively benign compared to iron overload, based on the recent description of the Verona mutation in which an L-ferritinemia occurs related to a genetic mutation in the IRE [Girelli et al., 1995a, supra). Ferritin mRNA with an inactive/deleted IRE appears to be stable and functional based on data obtained both in vitro [Dickey et al., 1988, supra; Dix et al., 1992, supra] as well as being active in vivo [Girelli et al., 1995b, supra].

Transition metal complexes (TMCs) have the potential to specifically inactivate the ferritin-IRE in cells; the result could also be extended to inactivate other mRNAs. TMCs can be prepared as stable molecules with rigid, three dimensional shapes. Studies of the ferritin IRE structure in solution have shown that TMCs can cleave the ferritin IRE at specific sites. As shown herein, the IRE in ferritin mRNAs could be inactivated by TMCs in situ, therefore drugs based on TMCs can be developed to increase ferritin synthesis in cases of potential iron overload. IRE-specific TMCs are selected by classical and combinatorial synthesis. Identification of other mRNAs as targets for TMCs use SELEX with a TMC as the fixed ligand and polyA$^+$ RNA as the source of variable sequences.

IREs are 28–30 nucleotides long. All have a conserved sequence in the middle, CAGUGX, and C 4–5 residues on the 5' side of the CAGUGX. The secondary structure of all IREs is a hairpin loop (FIG. 1) with an internal loop of 4 nucleotides (ferritin) or predicted bulge (TfR-IREs and the eALAS-IRE). All IREs bind members of an IRE-specific regulatory protein family, the IRPS; currently two IRPs have been identified [Iwai, 1995, supra; Guo et al., *J. Biol. Chem.*, 268: 24252–24260 (1994); Samaniego et al., *J. Biol. Chem.*, 269: 30904–30910 (1994)].

A summary of the types of information obtained by probing the ferritin-IRE region with existing TMCs is shown in Table 1. Enhanced specificity of TMC targeting to the ferritin-IRE or other regulatory elements result from the more systematic approaches proposed here. The heteroaromatic TMC ligands studied with the IRE are (phen)$_2$phi, (tpy)bpy, and (phen)$_2$ or 1,10-phenanthroline. (Phen)$_2$phi which binds in the major groove of a DNA B-helix is too large for the narrow groove in A-form RNA. (Phen)$_2$phi binds to t-RNA$^{phe}$ or regions of 5S RNA occurs where helices are distorted either by non-Watson-Crick base pairs, or tertiary interactions [Chow et al., 1992, supra]. (Tpy)bpy appears to react only with sugar residues in the RNA chain that project into the solvent, outside a folded RNA structure [Neyhart et al., *J. Am. Chem. Soc.*, 117: 1463–1471 (1995)]. (Phen)$_2$ or 1,10-phenanthroline binds in the major groove of DNA, but in RNA appears to insert between stacked bases at regions distorted by internal loops [Murakawa et al., 1989, supra; Hermann and Heuman, *RNA*, 1: 1009–1007 (1995)]. Fe-bleomycin is a glycopeptide which has a more flexible shape in contrast to the heteroaromatic TMCs. The ferritin-IRE region has Fe-bleomycin sites which revealed long range interactions between the IRE and the FL in ferritin mRNA, and a site in a TfR-IRE that was absent in the ferritin-IRE (30-mer). As an antitumor drug Fe-bleomycin establishes the efficacy of one TMC as therapeutic agent. The main cellular target of Fe-bleomycin is DNA, but the existence of RNA sites in vitro indicates the possibility of an RNA target in rare cases.

The selectivity of reaction of TMCs and IRE structure (Table 1) suggests a specific three dimensional RNA structure. Other observations which emphasize the specificity of IRE three dimensional structure include: (i) Poor reactivity of IREs, in native conformations, with protein RNAses that should cut either single or double-stranded regions [Harrell et al., 1991, supra; Bettany et al., *J. Biol. Chem.*, 267: 16531–16537 (1992)]; aberrant reactivity during alkylation [Wang et al., 1990, supra]; (ii) Specificity of regulator protein (IRP) binding [reviewed in Klausner et al., 1993, supra; Theil, 1994a, supra]. (iii) Differential imino proton exchange using D$_2$O and NMR spectroscopy [Sierzputowska-Gracz et al., 1995, supra]; (iv) Relationship of HL structure to IRP binding using mutagenesis of the loop [Henderson et al., 1994, supra; Butts et al., 1996, supra] and NMR spectroscopy [Sierzputowska-Gracz et al., 1995, supra]; and (v) Extremely high phylogenetic conservation of primary sequence and function within a type of IRE (96–99%); lower sequence conservation between IRE-types in the same animal (34–87%) (Table 2) [Theil, 1994a, supra].

The power of a combinatorial approach to finding specific RNA-ligand interactions, without information about either 2D or 3D RNA structure, was recently demonstrated with a mixture of randomly synthesized oligoribonucleotides. RNAs were selected for high affinity binding to theophylline, a bronchial dilator which requires close monitoring during use to avoid toxicity. RNAs with $K_d \sim 10^{-7}$M were identified, an affinity higher than that often observed with combinatorial mixtures of oligopeptides [Gold et al., 1995, supra]. Specificity of RNA-ligand interaction was demonstrated by the observation of a decrease in Kd of $10^{-4}M$ for caffeine, a monomethyl substituted theophylline [e.g., Jenison et al., 1993, supra]. The RNA aptamer has a 2D structure of a hairpin loop. A similar approach was used with to find RNA which distinguished between citrulline and arginine. The RNA aptamer has recently been shown to contain two asymmetric internal loops which stack and form triple base interactions around the ligand [Yang et al., Science, 272: 1343–1347 (1996)]. In contrast to the combinatorial experiments just described, where RNA structure was varied and the small organic molecule was defined (theophylline or arginine), the present protocols vary the organic molecules (TMCs) that recognize a specific RNA (the ferritin IRE), and emphasizes development, identification and use of a ligand binding to a specific RNA structure. [Note that the IRE sequences have already survived natural selection ("natural selex") over millions of years (Table 2).] The recent demonstration of how much evolutionary selection has occurred naturally with the IRE is a recent combinatorial experiment [Henderson et al., 1994, supra] i.e., testing of combinatorial mixtures of loop sequences, identified only one mutation which approached wild type RNA protein (IRP-1/IRP-2) specificity [Henderson et al., 1994, supra; Butts et al., 1996, supra].

Experimental protocols are provided herein to exploit the relationship between TMCs and the IREs of mRNAs. Such protocols provide clarification as to the structure and function of the ferritin IRE during changes in cellular iron metabolism and in addition lead to IRE-specific TMCs for enhancing ferritin synthesis for managing iron overload (thalassemia, sickle cell anemia and hemochromatosis). Further these protocols permit the targeting of specific TMCs towards other regulatory elements of mRNAs involved in other diseases.

MATERIAL AND METHODS

Construction of Vectors for TMC (transition metal complex) targeting of the IRE in HeLa Cells Plasmid pCMVp2b1z1 are used to insert the H ferritin IRE+FL and the L ferritin IRE+FL downstream from the CMV promoter and upstream from a β-gal reporter. L and H ferritin IRE+FL differ in the bases of the conserved triplet of base pairs in the FL (FIG. 1; Dix et al. [1993, supra]) and in the composition of the IRE lower stem (Table 2; Theil [1994a, supra]). The pCMVp2b1z1 plasmid is constructed from Stratagene plasmid pBK-CMV, by insertion of a LacZ sequence between the Nhe I and Hind III sites and insertion of the BIV-tar sequence in the Bam H I site upstream from the LacZ gene. Deletion of the BIV tar sequence from pCMVp2b1z1 is accomplished by EcoR1 and Nhe 1 digestion; the H ferritin IRE+FL or the L ferritin IRE+FL are inserted into the EcoR1 and Nhe 1 sites, upstream from the Lac Z sequence. The two IRE+FL sequences are synthesized as two sets of oligonucleotide sequences containing the H ferritin or L ferritin IRE+FL (FIG. 1) with sequences corresponding to the "sticky ends" of the digested Nhe1 and EcoR1 sites at each end. The complementary oligonucleotides of each pair are melted, annealed, ligated to the digested pCMVp2b1z1 vector, and transformed into HB101 for amplification. When necessary, FL deletion constructs are made with oligonucleotides containing just the H-ferritin IRE and the L-ferritin IRE (FIG. 1). All constructs are sequenced.

Purified (Qiagen) DNA is used to transfect HeLa cells.

Cells are cultured in DMEM medium (10% fetal bovine serum) and transfected with lipofectin (GIBCO), using OPTI MEM (GIBCO) medium and the conditions recommended by the supplier. Under such conditions transfection frequencies, using β-gal as the reporter, ranged from 25–40% (FIG. 5) and the amount of mRNA accumulated, that was encoded in the plasmid template, was sufficient to isolate using Qiagen Oligotex and to detect by primer extension analysis (FIG. 5).

Cleavage of mRNA by Transition Metal Complexes (TMCs) in vivo: transfection of HeLa cells or tadpole reticulocytes: Cells treated with Cu(phen)$_2$.

Cu(phen)$_2$ was added to HeLa cells in Eagle's DMEM 10% FBS medium 24 or 48 hours after transfection with pCMVp2b1Z1, which contains a BIV tar sequence upstream from a β-gal reporter; transfection efficiency was 25–40%. Reticulocytes were collected at 40–50% maturity and incubated in Amphibian Ringer's solution with amino acids [Shull and Theil, 1982, supra]. PolyA$^+$ RNA was isolated from the cells (Qiagen oligo-tex) and analyzed by primer extension; primers bound 20–40 nucleotides downstream from the region of interest [Wang et al., 1990, supra]. Cleavage sites were identified in the gel for the BIV-Tar mRNA in HeLa by calibration with dideoxysequencing cDNA reactions transcribed from the DNA.

Results

TMCs were reacted with the IRE in ferritin in mRNA and synthetic oligonucleotides in vitro and high specificity of interaction and sensitivity to changes in IRE structures were observed, though no design plan was used in selecting the TMCs [FIG. 3; Wang et al., 1990, supra; Harrell et al., 1991, supra; Dix et al., 1993, supra; Thorp et al., 1996, supra]. Earlier data also showed that ferritin mRNA with an inactive IRE had the same stability as other mRNAs in vitro [Dix et al., 1992, supra] and are active in vivo [Girelli et al., 1995, supra] and in vitro even when decapped [Dickey et al., 1988, supra]. An alternative study used a test TMC, Cu(phen)$_2$OH$^+$ (1,10 phenanthroline Cu), to demonstrate cutting of mRNA at specific sites with intact cells (cultured HeLa cells and tadpole reticulocyte suspensions) (FIG. 5). Phen(1,10-phenanthroline) was chosen as the model for design and development because the shape is rigid and the synthetic chemistry more completely defined; the bleomycin glycopeptide is flexible, the shape depends more on the metal that is bound, and the synthetic chemistry is more difficult.

Specificity of Interactions of IREs with Transition Metal Complexes (TMCs) in vitro Specificity of Cleavage of the ferritin IRE in vitro TMC cleavage of the IRE was initially studied in natural ferritin mRNA, using the polyA$^+$ fraction of embryonic (bullfrog tadpole) red cells. Ferritin mRNA is ~10% of total in embryonic red cells [Shull and Theil, 1982, supra]; the large size of bullfrog tadpoles (~5–15 g) provided a convenient source of embryonic red cells. A ferritin mRNA specific primer and reverse transcriptase were used to synthesize a collection of cDNA fragments that correspond to the cleaved RNA fragments. Separation of the fragments by electrophoresis in an urea acrylamide gel, calibrated with a set of dideoxynucleotide fragments, showed the cut sites or RNA protection [Table 2; Wang et al., 1990, supra; Harrell et al., 1991, supra]. The initial use of natural mRNA created a base line and the assurance that sites observed later in full length in vitro transcripts and oligomers correspond to the natural RNA [Dix et al., 1993, supra; Sierzputowska-Gracz, 1995, supra; Thorp et al., 1996, supra].

Site directed mutations in the IRE+FL region have been studied in capped, in vitro transcripts by measuring changes in translation rate and changes in reactivity with different TMCs. All the mutations studied with TMCs had decreased translational regulation. The specificity of recognition and sensitivity to mutation by TMCs for the IRE+FL was very high (FIG. 3), presumably due to the size/shape of the TMCs relative to RNA folds. Each of the TMC complexes used also cuts tRNA at specific folds sites. [Murakawa et al., 1989, supra; Carter et al., 1990, supra; Chow et al., 1992, supra]

The specificity of TMC shape/size on reactivity is illustrated with the wild type and mutant ferritin IREs, folded in the absence of magnesium. Among the 30 nucleotides in the ferritin IRE $Cu(phen)_2OH^+$ (1,10 phenanthroline Cu) cuts 2–3 sites; the sites, 24, 25 and the minor site at position 6 are all in the IL (FIGS. 1 and 4). Mutation IL-1, which increased the HL from 6 to 7 nucleotides and decreased the size of the IL from 4 to 2 nucleotides, eliminated the cut sites at 6, 24, 25 but mutation HL-1, which is G16A in the HL had no detectable effect on $Cu(phen)_2OH^+$ recognition. $Ru(tpy)bpyO^{2+}$ recognized only one site in the ferritin IRE, in the HL at position 14 (FIGS. 3 and 4); mutation IL-1, which increased the loop size, had two cleavage sites, both in the HL; mutation HL-1, which is simply a base substitution in the HL, displayed no change in reactivity with $Ru(tpy)bpyO^{2+}$. $Rh(phen)_2phi^{3+}$, the bulkiest TMC of the three bound no sites in the IRE itself, but cut a single site in the FL (IRE+FL 55 nucleotides), next to a conserved triplet of base pairs (TBP).

A triple mutation in the FL (FL-2), which disrupted the TBP (and diminished IRP repression [Dix et al., 1993, supra], eliminated the $Rh(phen)_2phi^{3+}$ site (many minor sites were observed indicative of multiple conformations of the IRE region). FL2R (a hextuple mutation which restored the TBP and full translational regulation and the TBP) also restored the $Rh(phen)_2phi^{3+}$ site, showing the correspondence between translational regulation and IRE+FL structure detected by cleavage with $Rh(phen)_2phi^{3+}$ [FIGS. 3 and 4; Thorp et al., 1996, supra].
Similarities and differences between ferritin and TfR IREs probed with TMCs in vitro.

Ferritin- and TfR-IREs differ in the number of G/C base pairs in the lower stem and in the IRP interactions (FIG. 2). Note in particular, the smaller amount of IRE/IRP complex formed for TfR IREc and poorer competition for IRP compared to the ferritin IRE (FIG. 2). The predicted secondary structure between the two helices in the stem also differs for the two IREs. The ferritin IRE has an internal loop (IL), (4 nucleotides) confirmed by reactivity with $Cu(phen)_2OH^+$ and dimethyl sulfate [Wang et al., 1990, supra]. The secondary structure of the TfR IRE predicts a single base bulge at the junctions of the two helices. Experimentally, TMC cleavage with $Cu(phen)_2OH^+$ showed a similarity in TfR IRE and ferritin IRE. There appears to be an internal loop in the TfR IRE of dimensions similar to the ferritin IRE. The predicted AU base pairs of the lower stem of the TfR IRE (Table 2) may be weak enough to allow a distortion large enough for $Cu(phen)_2OH^+$ binding and cleavage. On the other hand, IRE structural differences between the ferritin IRE and TfR IRE were detected: Fe bleomycin cut only the TfR IRE at position 4, (see FIG. 4B), and RNAse $T_1$ showed that HL structure of the TfR IRE at position 16 could be cut by RNAse $T_1$ in $3'$-$^{32}P$ RNA. Subtle structural differences between the TfR IRE and the ferritin IRE appear to be superimposed upon the overall structural similarity.

Reactivity of mRNA sequences with TMCs in whole cells

Embryonic (tadpole) Reticulocytes

Large amounts of ferritin mRNA occur naturally (~10% of the total, Shull and Theil, 1982, supra) in the reticulocytes of the embryonic red cell line. The accessibility of such cells in bullfrog tadpoles and the extensive amount of information about ferritin regulation and ferritin mRNA structure in the bullfrog model [Theil, 1994a, supra] make them a desirable choice for preliminary studies.

HeLa cells

Large amounts of a single species of mRNA can be produced in cultured mammalian cells by transfection with plasmids with very efficient promoters such as CMV. The ability to detect the mRNA encoded in the transfected DNA is illustrated in FIG. 5. Transfection frequencies, based on the detection of B galactosidase activity with X gal, were 25–40% (FIG. 5). HeLa cells are preferred because they are well characterized, easy to culture and display typical iron dependent regulation of ferritin expression [Cairo et al.s, 1985, supra], indicating that the trans factors required for ferritin IRE dependent regulation are present in HeLa cells.

The ability to detect the target mRNA by primer extension analysis was possible both in cultured HeLa cells and in cell suspensions of reticulocytes from tadpoles. $^{32}P$ primers were selected to bind 20–40 nucleotides downstream from the BIV tar mRNA, transcribed after transfection of HeLa cells with DNA of pCMVp2b1z1, or from the IRE in ferritin IRE in endogenous mRNA of tadpole red cells. [Reticulocytosis had been induced by injection of phenylhydrazine as previously described (FIG. 5; Shull and Theil, 1982, supra).] Such results confirm the large amount of ferritin mRNA in tadpole reticulocytes and show the large amounts of mRNA that were produced from transfected DNA in HeLa cells.

Cleavage of the target mRNA by $Cu(phen)_2OH^+$ (1,10-phenanthroline-Cu) also occurred in both cells types (FIG. 5). In the BIV tar LacZ mRNA, when probed upstream from tar flanking sequence, a single cleavage site was observed near the junction of the tar vector sequence at a C residue (FIGS. 5A, 5B); a transcription stop site occurred in the control RNA, at the same site in a small fraction of the mRNA molecules. No full-length mRNA remained in the Cu(phen) treated HeLa cells. Two sites were observed to be cleaved in the endogenous ferritin mRNA (FIG. 4B), but the gel was not calibrated. During the incubation with the TMC, no cell lysis occurred, but based on trypan blue exclusion ~40% of the HeLa cells were damaged. Such damage likely occurs because of the low specificity of the test TMC, this is minimized by increasing the selectivity of the TMC.

Discussion

Ferritin concentrates iron for normal cell use and for detoxification during iron overload. Expression of ferritin depends on the translation of stable ferritin mRNA, regulated by the noncoding iron responsive element (IRE). Factors which specifically affect IRE-dependent translation of ferritin mRNA include initiation factors, the iron regulatory protein (IRP), and the amount of iron in the cell. During iron overload, ferritin synthesis increases, but the amount of iron to be handled can exceed ferritin capacity which can result in toxic consequences. If the ferritin capacity of the body could be increased, then the body iron burden could also be safely increased (e.g., resulting in hyperferritinemia) leading to a potentially more positive outcome for long-term transfusion therapy. That hyperferritinemia is not likely to be toxic is suggested by the relatively benign effects (compared to iron overload) observed in the L-hyperferritinemia caused by a familial mutation (Verona) that inactivates the IRE an that H-ferritinemia is associated with responses to inflammation. Therefore, protocols are provided herein for probing ferritin IRE structure in mammalian cells, and for developing compounds for selective inactivation of the ferritin-IRE. The products obtained from these methods also is used in the study of the effects of iron and IRE-inactivation on ferritin expression. In addition the methods provided herein may be applied for regulatory elements in general including those particularly important in disease.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method of selecting a transition metal complex (TMC) that modulates the translation of an mRNA by selectively cleaving a regulatory element of the mRNA in a eukaryotic cell comprising:

A. contacting a candidate TMC with a eukaryotic cell that contains an mRNA that has an elected regulatory element which functions as a regulatory site for the translation of the mRNA;

B. determining a cleavage activity of the candidate TMC for the elected regulatory element;

C. determining the degree of disruption of normal cellular functions in the eukaryotic cell; and D. correlating said cleavage activity with the degree of disruption, wherein a chosen TMC is selected for having a maximal cleavage activity in a eukaryotic cell with a minimal degree of cellular disruption.

2. The method of claim 1 wherein determining said cleavage activity is performed by determining the amount of protein expressed by the mRNA; and wherein correlating said cleavage activity with the degree of disruption is performed by correlating the amount of protein expressed with the degree of disruption.

3. The method of claim 2 wherein the protein expressed by the mRNA is a marker protein.

4. The method of claim 1 wherein said degree of disruption of normal cellular functions is determined by evaluating a property of the eukaryotic cell selected from the group consisting of determining cellular poly $A^{30}$ integrity, determining cellular DNA integrity, quantifying cellular protein synthesis, quantifying cell growth, and evaluating cell viability as determined as a percentage of trypan blue exclusion.

5. The method of claim 1 further comprising:

E. administering the chosen TMC to a non-human animal containing an mRNA comprising the elected regulatory element; and F. determining the relative specificity of the chosen TMC to cleave the elected regulatory element relative to its disruption of normal cellular functions in the non-human animal; and wherein a selected TMC is selected on the basis of its ability to cleave the elected regulatory element while causing a minimum disruption of the normal cellular functions in the non-human animal.

6. The method of claim 5 wherein the non-human animal is a mouse.

7. The method of claim 1 comprising:

(a) contacting a TMC with an mRNA containing the elected regulatory element and an mRNA containing a control regulatory element; and (b) determining in vitro the relative specificity of the TMC for cleaving the elected regulatory element in comparison to cleaving the control regulatory element; wherein a candidate TMC is selected over an alternative TMC on the basis of the candidate TMC having a higher relative specificity than the alternative candidate TMC.

8. The method of claim 1 wherein the elected regulatory element is a first iron response element (IRE) and the control regulatory element is a second IRE.

9. The method of claim 1 wherein the organic ligand is selected from the group consisting of a phenanthroline and a phenanthroline derivative.

10. The method of claim 7 wherein the elected regulatory element is a first IRE and the control regulatory element is a second IRE.

11. The method of claim 10 wherein the first IRE is a ferritin IRE.

12. The method of claim 11 wherein the ferritin IRE is selected from the group consisting of H-ferritin IRE and L-ferritin IRE; wherein the ferritin IRE includes the ferritin specific, base paired IRE flanking region.

13. The method of claim 12 wherein the second IRE is a transferrin receptor IRE.

14. The method of claim 7 further comprising:

(c) varying the organic ligand and repeating steps (a) and (b).

15. The method of claim 14 further comprising:

(d) determining in vitro the relative specificity of the candidate TMC to cleave an mRNA comprising the elected regulatory element relative to a collection of nucleic acids selected from the group consisting of polyA$^+$ RNAs and plasmid DNAs; wherein a candidate TMC is selected on the basis of its ability to cleave the elected regulatory element while causing a minimum of cleavage of the collection of nucleic acids.

16. The method of claim 1 wherein the eukaryotic cell is an embryonic tadpole red cell.

17. The method of claim 1 wherein the eukaryotic cell is a mammalian cell.

18. The method of claim 17 wherein the mammalian cell is a HeLa cell.

19. A method of selectively enriching for a collection of cDNAs that comprise a regulatory element with a binding affinity for an elected TMC comprising:

(a) incubating a collection of mRNAs with an elected TMC wherein the elected TMC:
  (i) comprises an organic ligand and an non-oxidative metal; and
  (ii) is attached to a solid support matrix;
wherein the collection of mRNAs consists of mRNAs that comprise a regulatory element with a binding affinity for the elected TMC, and mRNAs that do not comprise the regulatory element with a binding affinity for the elected TMC;

(b) removing the mRNAs that do not bind the elected TMC;

(c) eluting the mRNAs that do bind the elected TMC; and (d) amplifying the eluted mRNAs by RT-PCR, therein forming a collection of cognate cDNAs which are enriched for cDNAs that comprise a regulatory element with a binding affinity for the elected TMC.

20. A method of selectively enriching for a collection of cDNAs that comprise a regulatory element with a binding affinity for an elected TMC comprising:

(a) incubating a collection of mRNAs anaerobically with an elected TMC, wherein the TMC:
  (i) comprises an organic ligand and an oxidative metal; and
  (ii) is attached to a solid support matrix;
wherein the collection of mRNAs consists of mRNAs that have a regulatory element with a binding affinity for the elected TMC, and mRNAs that do not have the regulatory element with a binding affinity for the elected TMC;

(b) removing under anaerobic conditions the mRNAs that do not bind the elected TMC;

(c) eluting under anaerobic conditions the mRNAs that do bind the elected TMC; and (d) amplifying the eluted mRNAs by RT-PCR, therein forming a collection of cDNAs enriched for cDNAs that comprise a regulatory element with a binding affinity for the elected TMC.

21. A transition metal complex (TMC) selected by a process comprising:

(a) contacting a TMC with a ferritin iron response element (IRE) and a transferrin receptor IRE; wherein the TMC comprises an organic ligand and an oxidative metal;

(b) determining in vitro the relative specificity of the TMC to cleave the ferritin IRE relative to the transferrin receptor IRE; wherein a candidate TMC that cleaves the ferritin IRE with specificity relative to the transferrin receptor IRE is selected;

(c) enhancing the specificity of the candidate TMC by varying the organic ligand and determining its relative specificity for the ferritin IRE relative to the transferrin receptor IRE; wherein the variation of the organic ligand is based, at least in part, on corresponding structural studies of the ferritin IRE; and wherein an enhanced TMC is selected for enhanced specificity for the ferritin IRE;

(d) determining in vitro the relative specificity of the enhanced TMC to cleave an mRNA comprising the ferritin IRE relative to a collection of nucleic acids selected from the group consisting of polyA$^+$ RNAs and plasmid DNAs; wherein an elected TMC is selected on the basis of its ability to cleave the ferritin IRE while causing a minimum of cleavage of the collection of nucleic acids;

(e) contacting an elected TMC with a eukaryotic cell containing an mRNA comprising the ferritin IRE;

(f) determining the relative specificity of the elected TMC to cleave the ferritin IRE relative to its disruption of normal cellular functions in the eukaryotic cell; wherein a chosen TMC is selected on the basis of its ability to cleave the ferritin IRE while causing a minimum disruption of normal cellular functions in the eukaryotic cell;

(g) administering the chosen TMC to a non-human animal containing an mRNA comprising the ferritin IRE; and (h) determining in the non-human animal the relative specificity of the chosen TMC to cleave the ferritin IRE relative to its disruption of normal cellular functions in the non-human animal; wherein the non-human animal contains the mRNA comprising a ferritin IRE; and wherein a selected TMC is selected on the basis of its ability to cleave the ferritin IRE while causing a minimum disruption of the normal cellular functions in the non-human animal.

22. A method of treating an animal subject having elevated levels of iron comprising administering a therapeutic amount of the selected TMC of claim 21; wherein the ferritin IRE functions as a negative regulatory site for the translation of the mRNA encoding ferritin, and the selected TMC selectively cleaves the ferritin IRE, thereby impairing its function as a negative regulatory site which results in an increase in the concentration of cellular ferritin synthesis.

23. A pharmacutical composition comprising the selected TMC of claim 21 and a pharmaceutically acceptable carrier.

* * * * *